(12) United States Patent
Ninkov

(10) Patent No.: US 6,414,036 B1
(45) Date of Patent: Jul. 2, 2002

(54) COMPOSITION FOR TREATMENT OF INFECTIONS OF HUMANS AND ANIMALS

(75) Inventor: Dusan Ninkov, Orange City, IA (US)

(73) Assignee: Van Beek Global/Ninkov LLC, Orange City, IA (US)

(*) Notice: Subject to any disclaimer, the term of this patent is extended or adjusted under 35 U.S.C. 154(b) by 0 days.

(21) Appl. No.: 09/499,197

(22) Filed: Feb. 7, 2000

Related U.S. Application Data

(60) Provisional application No. 60/151,858, filed on Sep. 1, 1999.

(51) Int. Cl.⁷ ................................................ A61K 31/05
(52) U.S. Cl. ........................................................ 514/731
(58) Field of Search .......................................... 514/731

(56) References Cited

U.S. PATENT DOCUMENTS

| | | |
|---|---|---|
| 3,692,916 A | 9/1972 | La Barbera |
| 3,966,779 A | 6/1976 | Satzinger et al. |
| 4,130,638 A * | 12/1978 | Dhabhar et al. ............... 424/55 |
| 4,380,506 A | 4/1983 | Kimura et al. |
| 4,985,465 A | 1/1991 | Hendler ...................... 514/712 |
| 4,992,276 A | 2/1991 | Dills et al. |
| 5,061,491 A | 10/1991 | Deryabin |
| 5,158,774 A | 10/1992 | Inman |
| 5,733,530 A | 3/1998 | Bacca et al. |
| 5,801,153 A | 9/1998 | Badaway |
| 5,891,422 A * | 4/1999 | Pan et al. ...................... 424/49 |
| 5,955,086 A | 9/1999 | DeLuca et al. .......... 424/195.1 |
| 5,965,518 A * | 10/1999 | Nakatsu et al. ................. 512/1 |
| 5,980,903 A | 11/1999 | Pruthi et al. |
| 5,990,178 A | 11/1999 | Ninkov |
| 6,010,993 A * | 1/2000 | Romano et al. ............ 510/309 |
| 6,106,838 A | 8/2000 | Nitsas |

FOREIGN PATENT DOCUMENTS

| | | |
|---|---|---|
| DE | 1 692 045 A | 5/1971 |
| DE | 3 511 862 A | 10/1986 |
| EP | 0 424 534 A1 | 5/1991 |
| FR | 2 467 601 A | 5/1981 |
| FR | 2 616 327 A | 12/1988 |
| FR | 2 618 670 A | 2/1989 |
| FR | 2 625 677 A | 7/1989 |
| FR | 2 706 770 | 12/1994 |
| FR | 2 715 848 A1 | 8/1995 |
| GB | 916439 | 1/1963 |
| JP | 53-66420 | 6/1978 |
| JP | 57-056416 A | 4/1982 |
| JP | 59-029620 A | 2/1984 |
| JP | 40-63579 A | 2/1992 |
| JP | 42-78070 A | 10/1992 |
| JP | 72-67873 A | 10/1995 |
| JP | 80-20510 A | 1/1996 |
| KR | 9 402 650 B1 | 3/1994 |
| RO | 80 355 A | 11/1982 |
| RO | 108 766 B1 | 8/1994 |
| RU | 2 007 177 C1 | 2/1994 |
| RU | 2 008 013 C1 | 2/1994 |
| RU | 2 013 094 C1 | 5/1994 |
| SU | 1 796 188 A1 | 2/1993 |
| SU | 1 837 887 A3 | 8/1993 |
| WO | WO 96/37210 | 11/1996 |
| WO | WO 97/01348 | 1/1997 |

OTHER PUBLICATIONS

Guérin, et al., "Activité antifongique d'extraits végétaux á usage thérapeutique. II. Étude de 40 extraits sur 9 souches fongiques", *Annales Pharmaceutiques Francaises*, vol. 43, No. 1, pp 77–81 (1985).

*The Merck Index*, Twelfth Edition, Published by Merck Research Laboratories Division of Merck & Co., Inc., Whitehouse Station, NJ, pp. 308, 1604 (1996).

\* cited by examiner

Primary Examiner—Kevin E. Weddington
(74) Attorney, Agent, or Firm—Merchant & Gould PC

(57) ABSTRACT

This disclosure provides pharmaceutical compositions which include oil extract from plants from the Labiatae family. In particular, the compositions can be formulated by combining extracts of essential oils from plants of the Labiatae family with an organic acid or a Group I salt. It is believed that the antimicrobial activity of the pharmaceutical composition is due to the presence of organic phenols, such as isopropyl-o-cresol, in the oil extract from the plants.

23 Claims, 9 Drawing Sheets

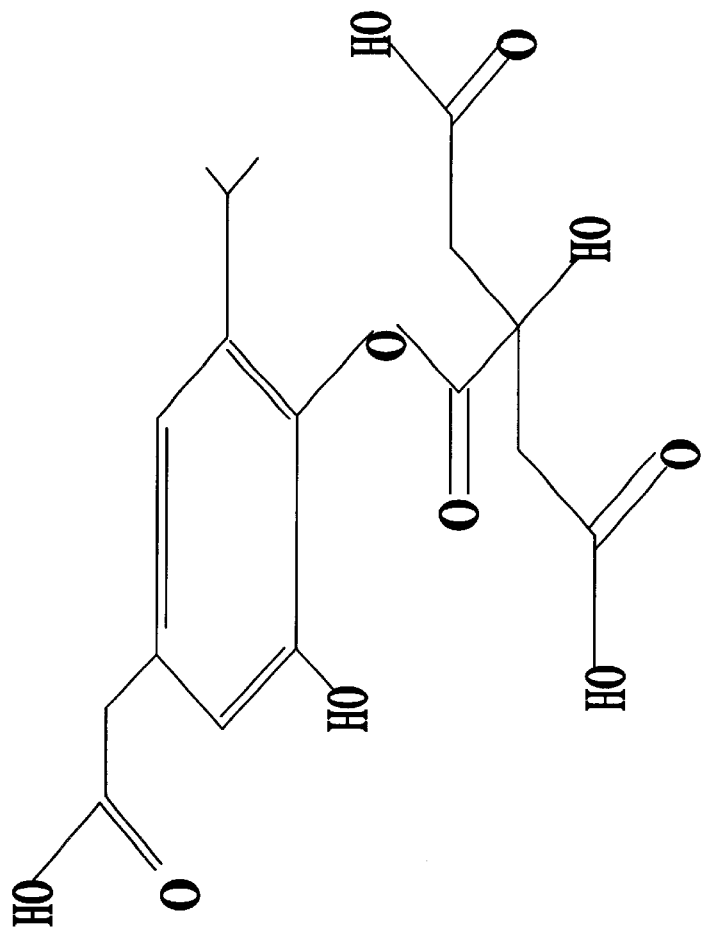
FIG.2
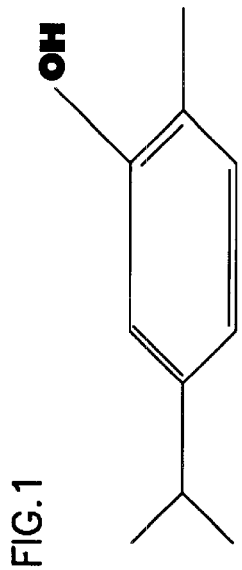
FIG.1   ISOPROPYL-O-CRESOL

FIG.3
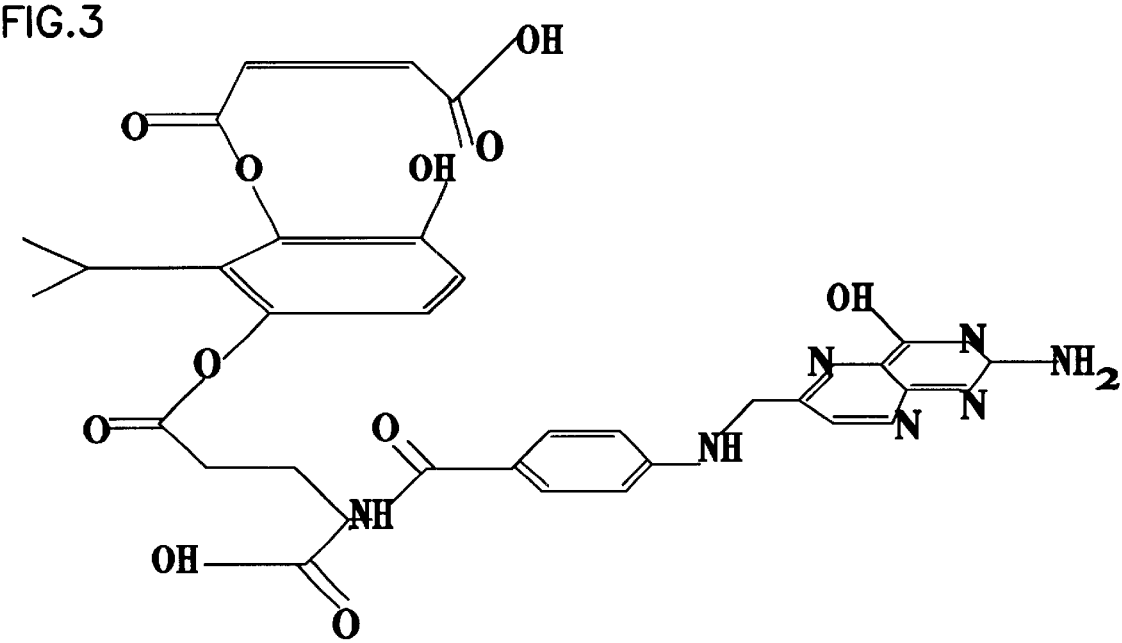
FIG.4
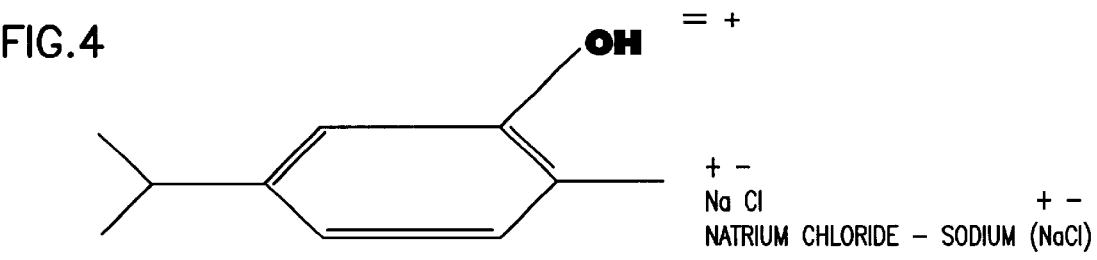
ISOPROPYL-O-CRESOL
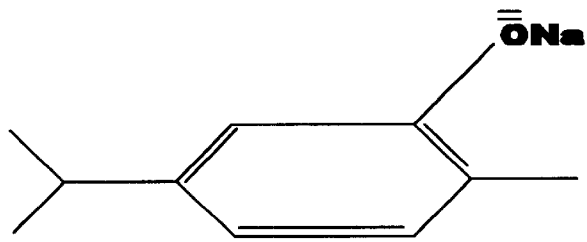
SODIUM PARA CRESOL FIG.5
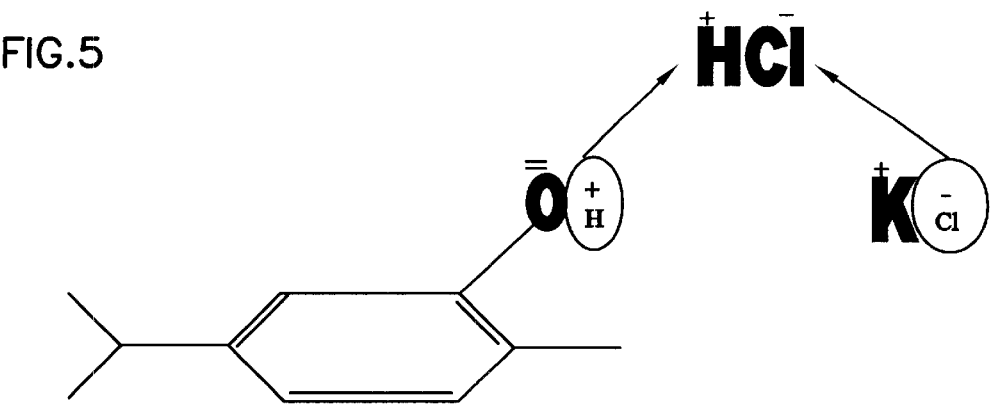
ISOPROPYL-O-CRESOL
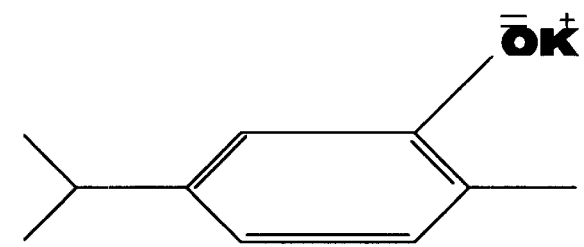
POTASSIUM PARA CRESOL
FIG.6
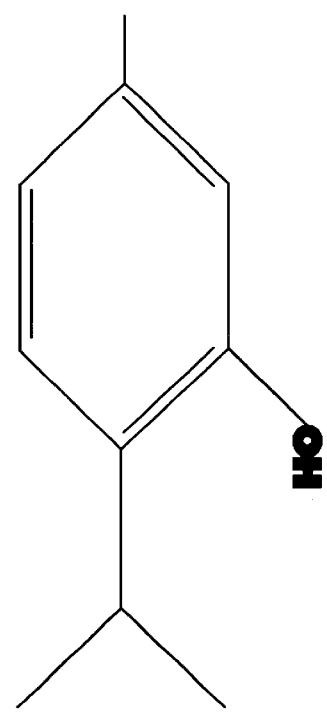

FIG.7
PHASE ONE:
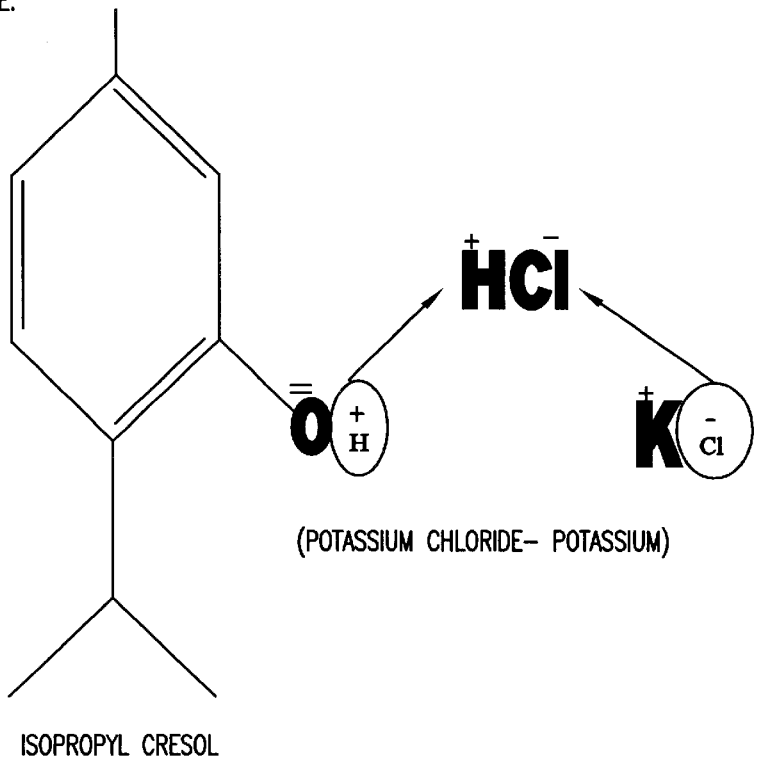
ISOPROPYL CRESOL
(POTASSIUM CHLORIDE− POTASSIUM)
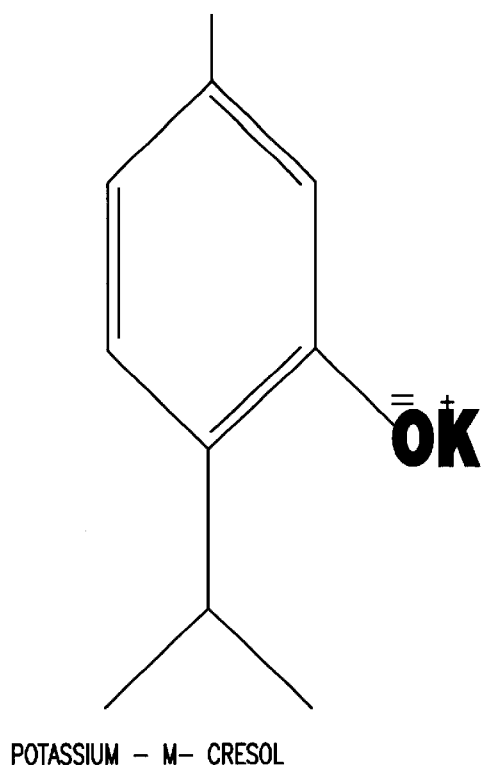
POTASSIUM − M− CRESOL

FIG.8
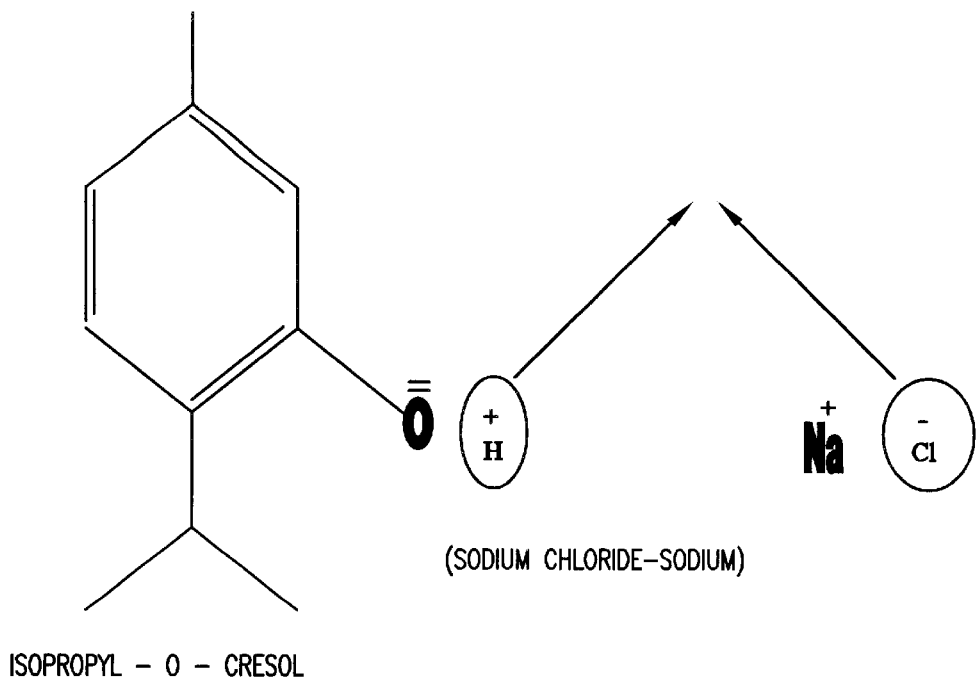
ISOPROPYL – O – CRESOL
(SODIUM CHLORIDE–SODIUM)
PHASE TWO:
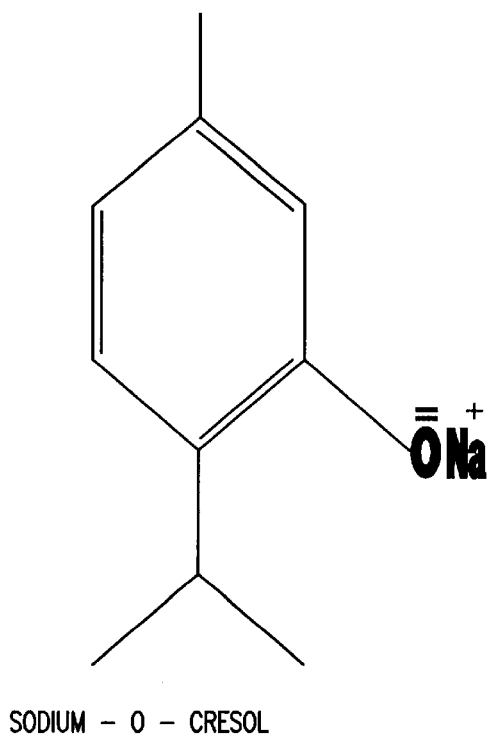
SODIUM – O – CRESOL

COMPOSITION FOR TREATMENT OF INFECTIONS OF HUMANS AND ANIMALS This application claims priority to United State Provisional Application Serial No. 60/151,858, filed on Sep. 1, 1999, entitled CITRO-PROPIONO-CREOSOL AND FUMO-CREOSOL-FOLIN FOR THE TREATMENT OF INTERNAL AND EXTERNAL INFECTIONS OF HUMANS AND ANIMALS, the disclosure of which is incorporated by reference herein in its entirety.

FIELD OF THE INVENTION

The invention relates to pharmaceutical compositions which include oil extract from plants from the Labiatae and Verbenacea family.

BACKGROUND

The common name for members of the Labiatae, a large family of chiefly annual or perennial herbs, is the "mint family." The mint family is classified in the division Magnoliphyta, class Magnoliopsida, order Lamiales. The mint family includes about 200 genera, such as Salvia (sage), Rosmarinus (rosemary), Mentha (mint), Ocimum (basil), Thymus (thyme), Marrubium (hoarhound), Monarda (horse-mint), Trichostema (bluecurls), Teucrium, Hyptis, Physostegia, Lamium (henbit), Stachys, Scutellaria (skullcap), Nepeta (catmint). Members of the Verbenaceae family include Lippia (Mexican Oregano) and Lycopus.

The plants in the mint family are typically shrubby or climbing forms, although some exist as small trees. The plants are found throughout the world.

The mint family is well known for the aromatic volatile or essential oils in the foliage, which are used in perfumes, flavorings, and medicines. Among the more important essential oils are those derived from sage, lavender, rosemary, patchouli, and the true mints. Many of the commonly used potherbs are from the mint family, e.g., basil, thyme, savory, marjoram, oregano, and the plants previously mentioned.

Many of these plants have a history of medicinal use in domestic remedies, such as catnip, pennyroyal, hyssop, self-heal, the horehound of confectionery. Others are used as curative teas, for example, bee balm and yerba buena.

The true mints belong to the genus Mentha. Catnip or catmint refers to a strong-scented perennial herb (*Nepeta cataria*) of the family Labiatae. Catnip is native to Europe and Asia and naturalized in the United States. Although best known for its stimulating effect on cats, tea of the leaves and tops of the catnip plant have long been used as a domestic remedy for various ailments. For example, dry leaves from *Nepeta cataria* have been used for the production of tea, used to treat restlessness, nervousness, insanity, and as a tonic for colic and carminative.

U.S. Pat. No. 5,990,178 discloses pharmaceutical compositions for treating a disease in poultry induced by hemoflagellates. The pharmaceutical compositions contain thymol (5-methyl-2[1-methylethyl]phenol) and/or carvacrol (5-isopropyl-2-methylphenol). Thymol (also referred to as isopropyl-cresol) and carvacrol (also referred to as Isopropyl-o-cresol) can be synthetic or obtained from oil extract from plants such as *Origanuum vulgaris, Thymus vulgaris, Mentha piperita, Thymus sepilum, Saturia hortensis, Saturea montana, Saturea subricata, Carum corticum, Thymus zugus, Ocimum gratisimum, Moranda pungata, Mosla jananoica,* and *Salva officinalis.*

WO 96/37210 discloses pharmaceutical compounds which contain etheric oils from plants including *Origanum vulgaris, Thymus vulgaris, Mentha piperita, Thymus serpilum, Saturea horensis, Saturea montana, Saturea subricata, Carum corticum, Thymus zugis, Ocimum gratisimum, Moranda pungtata, Mosla japanoica* and *Salva officinalis.*

SUMMARY

This disclosure provides pharmaceutical compositions which include oil extract from plants from the Labiatae and Verbenacea family. In particular, the compositions can be formulated by combining extracts of an essential oil with an organic acid or a Group I salt. It is believed that the antimicrobial activity of the pharmaceutical composition is due to the presence of organic phenolic compounds, such as isopropyl-o-cresol, (5-isopropyl-2-methylphenol) and/or isopropyl-cresol (5-methyl-2[1-methylethyl]phenol) in the oil extract from the plants.

Suitable plants from the Labiatae and Verbenacea family include, but are not limited to, Ocimum spp., Saturea spp., Monarda spp, Origanum spp, Thymus sop., Mentha spp., Nepeta spp., *Teucrium gnaphalodes, Teucrium polium, Teucrim divaricatum, Teucrim kotschyanum, Micromeria myrifolia, Calamintha nepeta, Rosmarinus officinalis, Myrtus communis, Acinos suaveolens, Dictamnus albus, Micromeria fruticosa, Cunila origanoides,* Mosla Japonoica Maxymowitz, *Pycnanthemum nudum,* Micromenia Juliana, *Piper betel, Trachyspermum ammi* and *Lippia graveolens.* In a preferred composition, the plant is *Nepeta racemosa* or *Nepeta Cataria.*

Examples of suitable organic acids include citric acid, propionic acid, fumaric acid, folic acid, malic acid, ortho-phosphoric acid, acetic acid, lactic acid, butyric acid, glutamic acid, aspartic acid, and formic acid. A preferred composition includes an organic acid such as citric acid, propionic acid, fumaric acid and folic acid.

Suitable Group I salts include salts formed from a Group I cation and halogen. Preferred salts include Group I chloride salts and the most preferred salts are sodium chloride and potassium chloride.

A number of different formulations can be manufactured depending on the type and location of the infection to be treated.

BRIEF DESCRIPTION OF THE DRAWINGS

FIG. 1 shows a structural formula for isopropyl-o-cresol or 2-methyl-5[1-methylethyl]phenol).

FIG. 2 shows a structural formula for 3-{4-(carboxymethyl)-2-hydroxy-6-isopropylphenoxy] carbonyl}-3-hydroxypentanedioic acid.

FIG. 3 shows a structural formula for (E)-4-[3-({4-[4-{[2-amino-4-hydroxy-7-pteridinyl)methyl]amino}benzoyl) amino]-4-carboxybutanoyl}oxy)-6-hydroxy-2-isopropylphenoxy]-4-oxo-2-butenoic acid.

FIG. 4 shows a structural representation of a chemical reaction between isopropyl-o-cresol and sodium chloride.

FIG. 5 shows a structural representation of a chemical reaction between isopropyl-o-cresol and potassium chloride.

FIG. 6 shows a structure for isopropyl-cresol (5-methyl-2[1-methylethyl]phenol).

FIG. 7 shows a structural representation of a chemical reaction between isopropyl-cresol and sodium chloride.

FIG. 8 shows a structural representation of a chemical reaction between isopropyl-cresol and potassium chloride.

DETAILED DESCRIPTION OF THE PREFERRED EMBODIMENT

Figure 9:
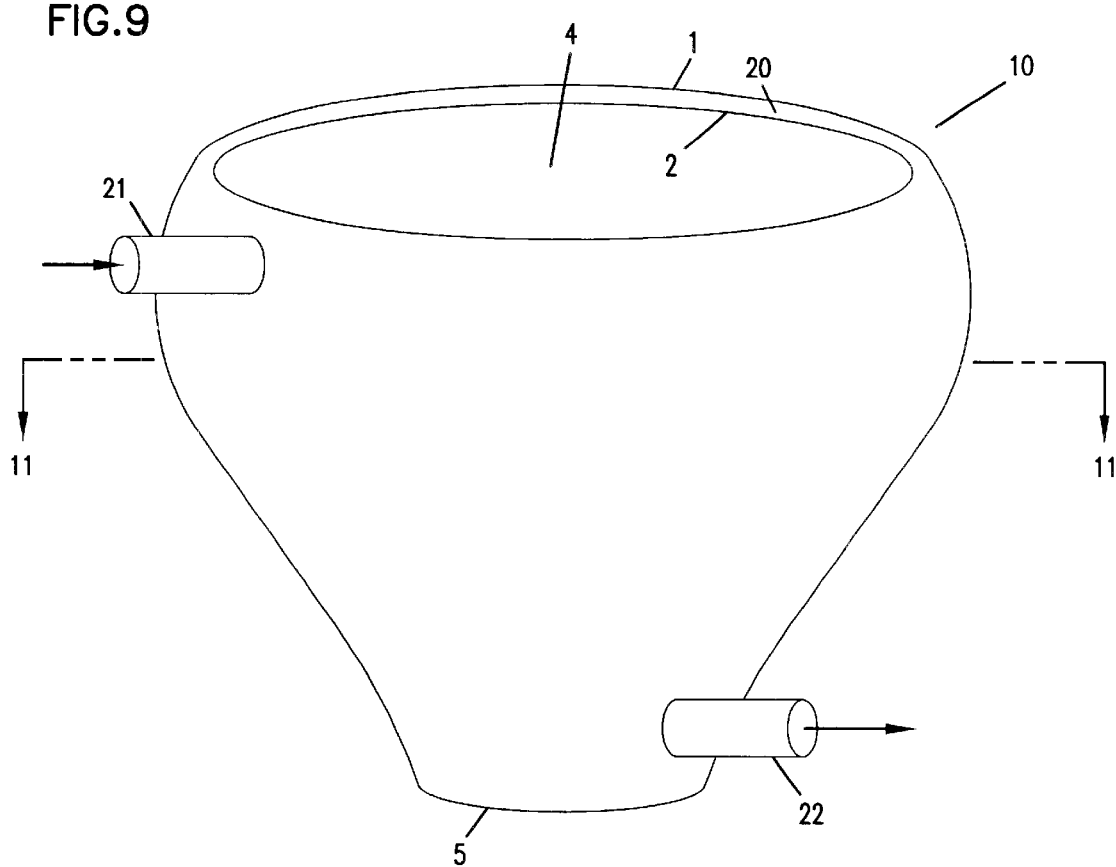
FIG. 9 shows an elevational view of a high speed mixer.

This disclosure provides pharmaceutical compositions which include oil extract from plants from the Labiatae and Verbenaceae family. In particular, the antimicrobial pharmaceutical compositions can be formulated by combining isopropyl-o-cresol (5-isopropyl-2-methylphenol) and/or isopropyl-cresol (5-methyl-2[1-methylethyl]phenol), obtained from plant oil extracts, with an organic acid or a Group I salt to form an antimicrobial compound.

The pharmaceutical compositions are suitable for treating internal and external microbial infections in animals, including, humans and livestock, including but not limited to horses, cows, pigs, sheep, goats, rabbits, dogs, cats and poultry, including, but not limited to chickens, turkeys, ducks and pet birds.

Because the antimicrobial compound is degraded by enzymes, the pharmaceutical compositions are particularly well suited for treating microbial infections in livestock. Little residue from the composition is found in products from treated livestock, such as milk, eggs, and meat. Organic phenolic compounds such as isopropyl-o-cresol and isopropyl-cresol are degraded by enzymes into inactive metabolites. The metabolites can be excreted in the urine (approx. 90%) or expired from the lungs (10%) in the form of $CO_2$. Additional information on the degradation of isopropyl-o-cresol and isopropyl-cresol, can be found in US Pharmacopoeia, British and European Pharmacopoeia, and *Textbook of Veterinary Physiology*, by Prof. Dr. James G. Cunningham, Ph.D., 2nd edition. The text of all three references is hereby incorporated by reference herein.

Additionally, the antimicrobial compound does not appear to be mutagenic or carcinogenic.

Furthermore, it is believed that the efficacy of the antimicrobial compound will not be compromised due to pathogen resistance. It is believed that the activity of the antimicrobial compound is similar to the activity of benzyl alcohol, phenol and polyphenols in that the antimicrobial compound destroys the cell membrane of the microorganism to cause cell death. The British Pharmacopoeia, Edition 1996 reports that microorganisms do not build resistance to benzyl alcohol, phenols, polyphenols, and similar products.

As used herein, the term "antimicrobial activity" includes bacteriocidal, fungicidal, protozoanicidal, and other disinfective activity.

I. Antimicrobial Compound
A. Organic Phenolic Compound

The antimicrobial compounds of the invention are made by reacting an organic phenolic compound such as isopropyl-o-cresol (5-isopropyl-2-methylphenol) or isopropyl-cresol (5-methyl-2[1-methylethyl]phenol) with an organic acid or a Group I salt.

Isopropyl-o-cresol is a crystal with a boiling point of about 233° C. at atmospheric pressure. Isopropyl-cresol is a liquid that has a boiling point at atmospheric pressure of 237–238° C. Both compounds volatilize in water vapor.

Organic phenolic compounds can be made synthetically by known methods, or can be obtained from plant oil extract. Preferably, the oil is extracted from a member of the Labiatae or Verbenaceae family. The Labiatae family includes about 200 genera, such as Salvia, Rosmarinus, Mentha, Ocimum, Thymus, Marrubium, Monarda, Trichostema, Teucrium, Hyptis, Physostegia, Lamium, Stachys, Scutellaria and Lycopus. Suitable plants include, but are not limited to, Ocimum spp., Saturea spp., Monarda spp, Origanum spp, Thymus spp., Mentha sp., Nepeta spp., *Teucrium gnaphalodes, Teucrium polium, Teucrim divaricatum, Teucrim kotschyanum, Micromeria myrifolia, Calamintha nepeta, Rosmarinus officinalis, Myrtus communis, Acinos suaveolens, Dictamnus albus, Micromeria fruticosa, Cunila origanoides*, Mosla Japonoica Maxymowitz *Pycnanthemum nudum*, Micromeria Juliana, *Piper betel, Trachyspermum ammi, Lippia graveolens* as well as others. In a preferred composition, the oil extract is from plant of the species Nepeta including, but not limited to *Nepeta racemosa* (catmint), *Nepeta citriodora, Nepeta elliptica, Nepeta hindostoma, Nepeta lanceolata, Nepeta leucophylla, Nepeta longiobracteata, Nepeta mussinii, Nepeta nepetella, Nepeta sibthorpii, Nepeta subsessilis* and *Nepeta tuberosa*.

Organic phenolic compounds such as isopropyl-o-cresol and isopropyl-cresol are soluble in lipids. It is believed that the antimicrobial activity of the organic phenolic compounds is due to the destruction of lipids in the microorganism cell membrane.

1. Synthetic Production of Organic Phenolic Compound

Methods for synthetically producing organic phenolic compounds such as isopropyl-o-cresol and isopropyl-cresol are known. See for example *Organic Chemistry* by Morrison & Boyd 2d ed. 1971 at page 815. Additionally, these compounds are available from chemical manufacturers and are listed in the Merck Index. However, it is generally preferred that the organic phenolic compound be extracted from plants instead of being chemically synthesized. Because phenol is used to synthesize isopropyl-o-cresol and isopropyl-cresol, the resulting product tends to contain residual phenol (less than 1%). It is generally undesirable to administer a composition containing phenol to an animal because phenol is highly mutagenic and carcinogenic.

2. Extraction of Isopropyl-o-Cresol from Plants i. Cultivating the Plant

Plants of the Labiatae and Verbenacea families are found throughout the world and are relatively easy to cultivate. To cultivate the plants, seeds, preferably those with a high percentage (e.g., at least about 70 wt %, more preferably at least about 80 wt %, of organic phenolic compound), are planted in fine loose soil, preferably in a sub-tropical climate. Hybrid seeds having a high percentage of organic phenolic compounds can be produced by known techniques. The seeds are then cultivated using known agricultural techniques, such as watering, and artificial fertilizing.

Because the leaves contain a high amount of oil upon blossoming, it is preferred that the plants be harvested soon after the plants begin to blossom. Preferably, the plants are harvested within 24 hours after blossoming, more preferably within 12 hours after blossoming. Most preferably, harvesting is undertaken early in the morning or late in the evening hours when the leaves are not exposed to the sun.

Because the majority of the oil is found in the leaves and blossoms of the plant, it is preferred that the leaves and blossoms be utilized in the extraction process. Use of other parts of the plant may increase impurities and decrease yield.

ii. Extracting Oil from the Plant

Oil containing organic phenolic compounds can be extracted from either dried or fresh plants, or both. If the plant is dried, the drying process is preferably undertaken in special drying houses that are constructed to allow constant, free circulation of air. Preferably, the harvested leaves and blossoms should not be exposed to direct sunlight, as exposure to sunlight may reduce the amount of active material present in the leaves.

To dry the product, the leaves and blossoms are arranged in layers of 20–25 cm thick. To promote uniform drying, the layers should be turned up-side-down either manually or mechanically four times a day during the first three days of drying. Generally, the leaves are dried for about 7 to 8 days.

After the leaves and blossoms are dried, the oil can be extracted by known methods, including distillation, for example, steam distillation. Preferably, the oil is extracted in a two stage distillation process (double distillation). Preferably, the oil is first extracted by steam distillation (at a temperature of about 100° C.) to remove most impurities. Typically, after the first steam distillation, the extracted oil contains about 3% to about 4% by weight isopropyl-cresol; about 60% to about 70% isopropyl-o-cresol and about 26% to about 37% by weight impurities.

The oil is then re-distilled at a temperature between about 180° C. to about 200° C. to remove additional impurities. Preferably, the redistillation is performed twice (double re-distillation). If a double re-distillation process is used, the oil typically has a purity of greater than 90%, more preferably greater than 95%, and even up to 99%. Although yield tends to be lower when a double distillation process is used, typically about 1 to 10 kilograms, more typically about 3 to 7 kilograms of oil, are obtained for every 100 kilograms of dried leaves and blossoms.

In a steam distillation process, the distillation column generally has two output tubes: one for oil (at the base of the column) and one for water vapor (at the top of the column). A water source is positioned under the leaves and blossoms and is heated to about 100° C. preferably under a pressure of about 20 bar to about 25 bar (increased pressure will tend to reduce the distillation time). The steam passes through the leaves and blossoms, thereby creating oil droplets. Because the water vapor is lighter than the oil droplets, the water droplets flow out of the output tube positioned at the top of the distillation column and the oil droplets flow out of the output tube positioned at the base of the distillation column. The distillation process is carried out for about 1 to about 5 hours, more typically about 2 to about 3 hours.

B. Organic Acid

The organic phenolic compound can be reacted with an organic acid to form an antimicrobial compound having enhanced antimicrobial activity when compared to the organic phenolic compound alone. As used herein, the term "organic acid" refers to non mineral acids such as carboxylic acids (i.e., acids containing —COOH group) including aliphatic acids, such as acetic and formic acid; aromatic acids, such as benzoic or salicylic acid; dicarboxylic acids (i.e., acids containing two —COOH groups) including oxalic, phthalic, sebacic, and adipic acid; fatty acids; and amino acids. Examples of suitable organic acids include citric acid, propionic acid, fumaric acid, folic acid, malic acid, orthophosphoric acid, acetic acid, lactic acid, butyric acid, glutamic acid, aspartic acid, and formic acid. A preferred composition includes an organic acid such as citric acid, propionic acid, fumaric acid and folic acid.

Examples of antimicrobial compounds formed by reacting an organic phenolic compound with organic acid include 3-{[4-(carboxymethyl)-2-hydroxy-6-isopropylphenoxy]carbonyl}-3-hydroxypentanedioic acid, formed by reacting isopropyl-o-cresol with citric acid and propionic acid, referred to herein as citro-propiono-cresol (CPC). Another antimicrobial compound includes (E)-4-[3-({4-[(4-{[(2-amino-4-hydroxy-2,3-dihydro-6-pteridinyl)methyl]amino}benzoyl)amino]-4-carboxybutanoyl}oxy)-6-hydroxy-2-isopropylphenoxy]-4-oxo-2-butenoic acid, formed by reacting isopropyl-o-cresol with fumaric acid and folic acid, referred to herein as fumo-cresol-folin (FCF). Specific methods of forming such antimicrobial compounds are provided below.

C. Group I Salt

Alternately, the organic phenolic compound can be combined with a salt, preferably a Group I salt. A Group I salt refers to an ionic molecule that has as its cation one of the elements in Group I of the periodic chart of elements. Preferred Group I salts include Group I chloride salts, most preferably the Group I salt is sodium chloride and/or potassium chloride. The Group I salt is combined with the organic phenolic compound to form an antimicrobial compound comprising the deprotonated organic phenolic compound associated with the Group I cation. Specific methods of forming these compounds of the invention are provided below.

It is believed that the sodium and potassium ions, along with the deprotonated organic phenolic compound readily pass through or destroy the cell membrane. The association of the organic phenolic compound with sodium or potassium appears to increase the rate of pathogen destruction.

Preferably, the salt is obtained from a natural source. As used herein, the term "natural" refers to a substance or mixture that occurs in nature that is not synthetic or manufactured. "Synthetic natural compound" refers to compounds that are synthesized but are identical to a natural product. For example, sodium chloride can be obtained from the ocean.

C. Reaction to form Antimicrobial Compound

As used herein, the term "antimicrobial compound" refers to compounds formed by reacting an organic phenolic compound extracted from a plant of the Labiatae and/or Verbenacae family with an organic acid or a salt. The antimicrobial compound may also be referred to as the "active ingredient." An "antimicrobial compound" may refer to a compound formed by chemically reacting isopropyl-o-cresol with citric acid and propionic acid (See, FIG. 2) or with fumaric acid and folic acid. (See, FIG. 3). Alternately, an "antimicrobial compound" may refer to a compound formed by chemically reacting isopropyl-o-cresol or isopropyl-cresol with sodium chloride (See, FIGS. 4 and 8) or with potassium chloride (See, FIGS. 5 and 7).

As used herein, the term "reacting" refers to a process in which the organic phenolic compound is chemically modified (as compared to the formation of a solution). In the formation of an antimicrobial compound with an organic acid, both the organic phenolic compound and the organic acid are chemically modified such that covalent bonds are formed to interconnect the molecules. In the formation of an antimicrobial compound with a Group I salt, the reaction of the organic phenolic compound involves the deprotonation of the alcohol moiety to form an aryl oxide anion which then associates with the Group I cation in solution.

To form an antimicrobial compound by reacting the organic phenolic compound with an organic acid, the organic phenolic compound may be combined with an organic acid and mixed under high shear conditions. High shear conditions can be generated by mixing with a high speed mixer, preferably at speeds between about 200 RPM (revolutions per minute) and 2000 RPM.

For example, an organic phenolic compound can be combined with an organic acid (typically a liquid, preferably with a purity of at least 80% by weight, more preferably with a purity of at least 90% by weight). Preferably, the resulting mixture contains about 100 parts organic phenolic compound and about 25 to about 100 parts organic acid, more preferably about 50 to about 100 parts organic acid. Alternately, a solution can be prepared that contains 100 parts organic phenolic compound, 25 to 50 parts of a first organic acid and 25 to 50 parts of a second organic acid.

The mixture is mixed in a high speed turbo mixer (described below) for about 1 to about 20 minutes, more preferably about 5 to about 15 minutes, more preferably about 10 to about 15 minutes at a speed of about 200 to about 2000 revolutions per minute, more preferably about 500 to about 2000 revolutions per minute, most preferably about 1500 to about 2000 revolutions per minute. It is believed that the high shear conditions of the high speed mixture aid in the formation of covalent bonds between the organic phenolic compound and the organic acid(s).

To increase the reaction rate, the reaction is preferably performed at an elevated temperature. Preferably, the reaction is performed at a temperature between about 60° C. and about 100° C., more preferably at a temperature between about 75° C. and about 80° C.

Additionally, an "antimicrobial compound" may refer to a compound formed by reacting an organic phenolic compound, such as isopropyl-o-cresol or isopropyl-cresol, and a salt, such as sodium chloride (See, FIGS. 4 and 8) or potassium chloride (See, FIGS. 5 and 7). Preferably, the reaction between the organic phenolic compound and the salt is carried out in solution. More preferably, to form an "antimicrobial compound" by reacting an organic phenolic compound and the salt, the salt is combined with a liquid carrier, preferably an alcohol to form an electrolyte solution. Although other alcohols such as methanol can be used, ethanol, most preferably food grade ethanol, is used to reduce toxicity upon administration. Preferably, the salt is combined with the liquid carrier at a ratio of about 30:70 to about 50:50 by weight, more preferably about 40:60 by weight.

Preferably, the electrolyte solution contains organic phenolic compound and sodium and/or potassium ion in a ratio of about 90:1 by weight, more preferably a ratio of about 95:5, most preferably a ratio of about 90:10.

The electrolyte solution is then mixed in a high speed mixer. Preferably, the reaction is performed in a high speed turbo mixer at a speed of about 500 RPM (revolutions per minute) to about 2000 RPM, more preferably about 1000 RPM to 2000 RPM, most preferably about 1500 RPM to about 2000 RPM. It is believed that the high speed turbine aids in the deprotonation of the hydroxyl group on the organic phenolic compound (to form an aryl oxide anion). The sodium or potassium cations then associate with the aryl oxide anion via an ionic bond to form an organic phenolic salt.

Preferably the organic phenolic compound and the salt are mixed at high speed for about 5 to 20 minutes, more preferably about 10 to about 15 minutes. Preferably the mixing process is performed for at least about 10 minutes to allow sufficient pressure to develop in the mixer to deprotonate the hydroxyl group on the organic phenolic compound.

Alternately, the antimicrobial compound (compounds formed using organic acid or a salt) can be formed using a more traditional synthetic method. For example, an antimicrobial compound which includes a sodium salt of the organic phenolic compound can be prepared using a more traditional synthetic method. For example, the organic phenolic compound can be mixed with a salt of a base (such as sodium hydroxide or potassium hydroxide for example) in an organic solvent (such as ether, methylene chloride, or dimethylsufoxide for example). The anionic moiety from the base extracts the proton from the organic phenolic compound to form the aryl oxide anion, which then associates with the cation (preferably sodium or potassium). The resulting organic phenolic salt is purified by extraction into an aqueous solvent.

II. Pharmaceutical Composition

The antimicrobial compound can be used alone, or as part of a pharmaceutical composition. As used herein, the term "pharmaceutical composition" refers to a composition which includes at least one antimicrobial compound and a pharmaceutically acceptable carrier.

The antimicrobial compounds can be prepared and administered in a wide variety of oral, parenteral and topical dosage forms.

Pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from about 1 wt % to about 20 wt %, more preferably about 2 wt % to about 10 wt %, most preferably about 3 wt % to about 5 wt % antimicrobial compound. Suitable solid carriers are magnesium carbonate, magnesium stearate, talc, sugar, lactose, pectin, dextrin, starch, gelatin, tragacanth, methylcellulose, sodium carboxymethyl cellulose, a low melting wax, cocoa butter, etc. The term "preparation" is intended to include the formulation of the active compound with the encapsulation material as carrier providing a capsule in which the active component (with or without other carriers) is surrounded by carrier, which is thus in association with it. Similarly cachets are included. Tablets, powders, cachets, and capsules, can be used as solid dosage forms suitable for oral administration.

Liquid form preparations include solutions, suspensions, and emulsions, for example, water or water-propylene glycol solutions for parenteral injection. Such solutions are prepared so as to be acceptable to biological systems (isotonicity, pH, etc). Liquid preparations can also be formulated in aqueous polyethylene glycol solution. Aqueous solutions suitable for oral use can be prepared by dissolving the antimicrobial compound in water and adding suitable colorants, flavors, stabilizing and thickening agents as desired. Aqueous suspensions suitable for oral use can be made by dispersing finely divided active component in water with viscous material, i.e., natural or synthetic gums, resins, methyl cellulose, sodium carboxymethyl cellulose and other known suspending agents.

Ointment preparations contain heavy metal salts of the antimicrobial compound with a physiologically acceptable carrier. The carrier is desirably a conventional water-dispersible hydrophilic or oil-in-water carrier, particularly a conventional semi-soft or cream like water dispersible or water soluble oil-in-water emulsion which may be applied to an affected surface with minimum discomfort. Suitable compositions may be prepared by merely incorporating or homogeneously admixing finely divided compounds with the hydrophilic carrier or base or ointment.

Preferably, the pharmaceutical composition is in unit dosage form. In such form, the preparation is subdivided into unit doses containing appropriate quantities of the antimicrobial compound. The unit dosage form can be a packaged preparation, the package containing discrete quantities of preparation, for example, packeted tablets, capsules, powders in vials or ampoules, and ointments in tubes or jars. The unit dosage form can also be a capsule, cachet, tablet, gel or cream itself or it can be the appropriate number of any of the packaged form.

The quantity of antimicrobial compound in a unit dose may be varied or adjusted from 1 mg to 1000 mg according to the particular application. The antimicrobial compounds are typically administered at an initial dosage of about 5 mg to about 50 mg per kilogram daily. The dosages, however, may be varied depending upon the requirements of the animal being treated, the severity of the condition being treated and the compound employed. Determination of the proper dosage for a particular situation is within the skill of the art. Generally, treatment is initiated with smaller dosages. Thereafter, the dosage is increased by small increments until the desired effect is obtained. For convenience, the total daily dosage may be divided and administered in portions during the day if desired.

For example, a formulation which includes sodium bicarbonate, ($Na_2HCO_3$) may be suitable for treating disorders associated with gastro-intestinal pH disorders or diarrhea.

A. Combinations

A pharmaceutical composition may include one type of antimicrobial compound, or a combination of antimicrobial compounds. For example; a combination containing 3-{[4-(carboxymethyl)-2-hydroxy-6-isopropylphenoxy] carbonyl}-3-hydroxypentanedioic acid (CPC), and (E)-4-[3-({4-[(4-{[(2-amino-4-hydroxy-2,3-dihydro-6-pteridinyl) methyl]amino}benzoyl)amino]-4-carboxy- butanoyl}oxy)-6-hydroxy-2-isopropylphenoxy]-4-oxo-2-butenoic acid (FCF), can be used. Advantageously, a pharmaceutical composition which contains a combination of antimicrobial compounds appears to decrease the pH in the intestines and thus enhance the efficacy of the antimicrobial compounds for treating intestinal disorders. Alternately, a pharmaceutical composition which includes both a sodium and a potassium salt of an organic phenolic compound can be used. Furthermore, a combination which includes an antimicrobial compound formulated with an organic acid and an antimicrobial compound formulated as an organic phenolic salt can be combined in a single pharmaceutical composition.

Most preferably, the pharmaceutical composition includes antimicrobial compounds formulated as both sodium and potassium salts of the organic phenolic compound. Preferably, the total amount of sodium and potassium organic phenolic salts make up approximately 1 wt % to about 20 wt %, more preferably about 2 wt % to about 10 wt %, most preferably about 3 wt % to about 5 wt % of the pharmaceutical composition. Preferably, the sodium and potassium salts of the organic phenolic compound are present in a ratio of between about 1:99 and 99:1 by weight, more preferably between about 40:60 and 60:40 by weight, most preferably about 50:50 by weight. The combination of antimicrobial compounds appears to have a synergistic effect.

As used herein, the term "synergistic effect" refers to a phenomenon whereby the effect of two or more compounds together is greater then the sum of their effects when used individually. For example, whereas a pharmaceutical composition containing 100 mg of an organic phenolic sodium salt to treat an infection in an animal, a pharmaceutical composition containing only 45 mg of organic phenolic sodium salt and 45 mg of organic phenolic potassium salt may be needed to treat the same infection in the same animal. An example of the synergistic effect of a combination of antimicrobial compounds is shown in Example 16.

To form the pharmaceutical composition containing a combination of a sodium and potassium organic phenolic salt (or a combination of two different antimicrobial compounds containing organic acids), a solution containing the desired ratio of antimicrobial compounds is mixed at room temperature (e.g., about 20° C. to about 30° C., more typically about 23° C. to about 28° C.) for about 1–10 minutes, preferably about 2–5 minutes at a speed of about 25–100 RPM, preferably 50–75 RPM.

B. Microencapsulation

Products based on essential oils, such as organic phenolic compounds, tend to be absorbed at a level greater than 90% in the small intestines. Therefore, most of the activity of such products tends to be localized in the stomach and/or small intestine. However, there are many microbial infections that occupy portions of the gastrointestinal tract beyond the small intestine. Therefore, it may be desirable to extend the activity of the essential oil based product into the large intestine.

Microencapsulation is one method that can help extend the activity of the antimicrobial composition throughout the entire gastro-intestinal tract (GIT). Microencapsulation is a micro-packaging technique which involves the coating of small particles of solids, liquid droplets, or dispersion of solids, within liquids. Microencapsulated antimicrobial compound may be used to treat infections located in the end of the small intestines (e.g., jejunum and/or ileum) and beginning of the large intestines (e.g., ascending colon and transverse colon). The microencapsulation prevents release of the active ingredients in the stomach or in the beginning of the small intestines (e.g., duodenum). If the antimicrobial compound is not microencapsulated, the acidic environment of the stomach will tend to break the association between the antimicrobial compound and most carriers in the pharmaceutical composition (such as dextrose, starch, etc.) and thereby activate the antimicrobial compound in the stomach.

For example, a microencapsulated form of the antimicrobial compound may be used to treat Cryptosporidia spp. infections and/or chronic enteritis in humans; Cryptosporidia infections in animals, *Lawsonia intracellularis* and *Treponema hyodesynteriae* infections in pigs, and others.

One example of a microencapsulation process includes encapsulating the antimicrobial compound in a multi walled capsule such that the layers of the wall dissolve as the capsule travels through the gastrointestinal tract. Thus, the components that make up each layer of the capsule wall are chosen based on the conditions in the specific region of the gastrointestinal tract in which they are desired to dissolve. For example, the pH along the gastrointestinal tract (GIT) varies: in the stomach, the pH is between 2 and 5; in the duodenum, 4 and 6; jejunum, 4 and 6; ileum, 6.5 and 7.5; caecum 5.5 and 6.5; colon, 6.5 and 7; and rectum, 6.5 and 7. Therefore, the components of the wall layers may differ depending on what type of an ailment is to be treated, or its location, and whether the final formulation is meant to treat humans or animals. Each layer of the wall may also contain the compound of the invention so that upon dissolution of that wall layer, it can be released to effectuate treatment of the ailment.

Suitable coating matrices include fatty acids, waxes, sugars, and shellac.

Figure 13:
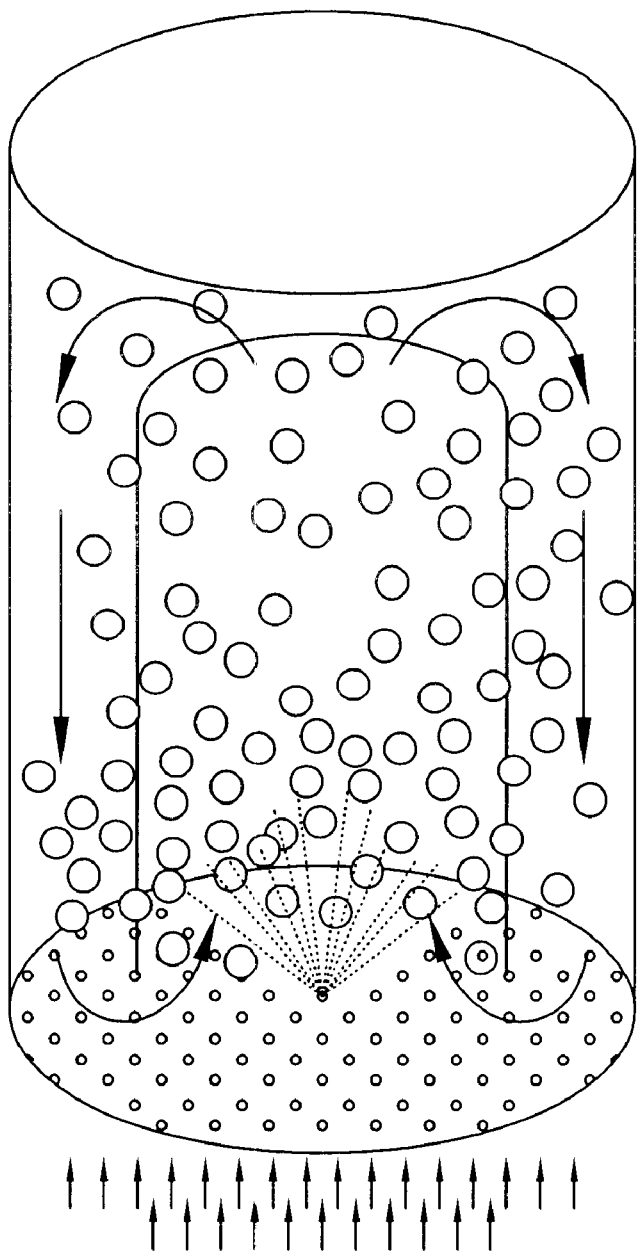
FIG. 13 shows an illustration of a fluidized bed process.

Encapsulation techniques are known. An example of one encapsulation technique (called fluidized bed coating) is provided below. In a fluidized bed, a suspension of solid particles is transformed into a fluidlike state by an upward gas flow through the system. Because of the intensive heat and mass transfer, fluidized bed reactors are widely used, e.g. in chemical industry for solid-catalyzed gas-phase reactions. To maximize the yield of such reactors, liquid reactants can locally be injected into the fluidized bed. The injected liquid reactants penetrate the fluidized bed and evaporate. For design purposes and the achievement of optimal operating conditions, the spatial distribution of the concentration of components and temperature has to be predicted. An illustration of the process is shown in FIG. 13.

Fluidized bed coating can be used to encapsulate the antimicrobial compound in a coating material which includes ethyl cellulose and plant oil. First, the antimicrobial compound described is combined in the fluid bed mixer with the ingredients to form a powder, such as the ingredients shown in the table below.

| Ingredient | Percentage by weight |
| --- | --- |
| Antimicrobial Compound | 10–15% |
| Corn Starch | 30–40% |
| Dextrose | 35–45% |
| Calcium Carbonate | 1–5% |
| Sodium Bicarbonate | 1–5% |
| Silicon Dioxide (SiO$_2$) | 1–5% |

The mixture is combined for about 10 to 30 minutes, preferably about 15 to 20 minutes at a temperature between about 75° C. and 100° C., more preferably between about 80° C. and 90° C. to form a powder.

After the powder is formed, a fatty acid composition can be added to the fluid bed mixer and mixed for about 5 minutes to about 20 minutes, more preferably about 10 minutes to about 15 minutes to form a fatty acid layer on the antimicrobial powder. Generally, the fatty acid is included in the mixer in an amount of about 20 wt % to about 25wt % fatty acid composition as compared to about 75 wt % to about 80 wt % antimicrobial powder.

After the fatty acid layer is formed, ethyl cellulose is added to the mixer and mixed for about 5 minutes to about 20 minutes, more preferably about 10 minutes to about 15 minutes, to form an ethyl cellulose layer. Ethyl cellulose is added to the mixer in an amount of about 20 wt % to about 25 wt % ethyl cellulose as compared to about suspension is formed by combining about 75 wt % to about 80 wt % coated antimicrobial powder.

As used herein, the term "fatty acid composition" refers to aliphatic monocarboxylic acids that can be liberated by hydrolysis from naturally occurring fats and oils. Fatty acids are predominantly straight-chain acids of 4 to 24 carbon atoms which may be saturated or unsaturated. The fatty acids are typically derived from plants, such as an oil seed, or animal sources, such as tallow. Examples of saturated fatty acids include palmitic and stearic acids. Examples of unsaturated fatty acids include oleic acid, and linolenic acid. Examples of suitable plant oils include rapeseed oil, corn oil, peanut oil, safflower oil, olive oil, soybean oil, sunflower oil, cottonseed oil, menhaden oil, herring oil, peanut oil, crambe oil, mustard oil, meadowfarm oil and canola oils.

Additional layers are formed by adding alternating rounds of fatty acid and ethyl cellulose to the mixer in the same manner as described previously. Preferably, the encapsulated antimicrobial compound is prepared with about 2 layers to about 10 layers, more preferably about 4 to about 6 layers. As used herein, "layer" refers to either a fatty acid layer or an ethyl cellulose layer. Thus, 2 layers would include 1 fatty acid layer and 1 ethyl cellulose layer. 6 layers would include 3 fatty acid layers and 3 ethyl cellulose layers. Generally, the resulting microcapulse has a diameter ranging from about 2 to about 5000 μm.

The microencapsulated product will allow a small liberation (about 20wt % to about 30wt %) of antimicrobial compound (active ingredient) in the stomach with the remainder being released in the small intestine, ileum and even in the colon depending on the specific compounds and number of layers used.

C. Additives

The pharmaceutical composition may also contain additives such as preservatives, vitamins, minerals, and amino acids. Suitable additives may vary depending on the desired end use for the pharmaceutical composition. For example, the pharmaceutical composition may contain additives such as vitamins and/or minerals. Examples of vitamins that may be included in the pharmaceutical composition include vitamins A, D, E and C. Examples of elements that may be included in the pharmaceutical composition include Sodium (Na), Potassium (K), Calcium (Ca), Magnesium (Mg), Manganese (Mn), Cobalt (Co), Zinc (Zn) and Copper (Cu). Additionally, amino acids such as glycine, methionine, lysine, and threonine may be included in the pharmaceutical composition.

D. Illustrative Pharmaceutical Compositions Containing Antimicrobial Compound for Administration to Humans A number of different formulations of the Antimicrobial Compound are possible. For example, the composition can be formulated as a capsule, tablet, syrup, tonic or liquid form.

Capsule

To form a capsule for release of the antimicrobial compound in the intestine (rather than the stomach), the antimicrobial compound is first prepared as a powder and encapsulated. To form a powder, the antimicrobial compound is combined with the ingredients in the relative amounts shown in the Table below.

| Ingredient | Percentage by weight |
| --- | --- |
| Antimicrobial Compound | 10–15% |
| Corn Starch | 25–35% |
| Dextrose | 40–50% |
| Calcium Carbonate | 1–5% |
| Sodium Bicarbonate | 1–5% |
| Other* | 1% |
| Silicon Dioxide (SiO$_2$) | 1–5% |

*Includes vitamins, minerals, amino acids and other additives

The ingredients are combined in the order shown in the table. After each ingredient is added, the combination is mixed for 3 minutes at 500 RPM. To form the capsule, the encapsulated powder is then combined with a binder such as dextrose and potato starch in the amounts shown in the Table below.

| Ingredient | Percentage by weight |
|---|---|
| Encapsulated Powder | 10–15% |
| Dextrose | 35–45% |
| Potato Starch | 45–55% |

After the capsule is formed, it may be encapsulated with a coating material. An illustrative coating material includes ethyl cellulose and soy bean oil.

A 500 mg capsule (containing the ingredients in the ratio shown in the table above) can be formulated and used to treat infections of the digestive tract in humans. An illustrative dosing regimen includes administering one 500 mg capsule daily to children (up to 12 years old) or two 500 mg capsules to adults every 8 hours.

Tablet

Tablets may be formulated by combining the encapsulated powder described above with dextrose, potato starch and colloids in the amounts shown in the Table below. Colloids are neutral ingredients which act as a "glue" to hold the active ingredients together.

| Ingredient | Percentage by Weight |
|---|---|
| Encapsulated powder | 10–15% |
| Dextrose | 35–45% |
| Potato Starch | 35–45% |
| Colloids | 10–15% |

The tablet may also include other carriers such as ethylcellulose or lactose. In one illustrative formulation, a 500 mg tablet may be formulated and used to treat digestive tract ailments in humans by administering 1 tablet daily to children up to 12 years of age, and two tablets every 8 hours for adults, until symptoms such as diarrhea subside.

Slow Release Formulation—Tablet

The tablet form of the antimicrobial compound can be prepared as a slow release formulation, for example, for treating urinary tract infections. An illustrative slow release formulation contains additional ethyl cellulose (5% more than previous formulation) to enhance activity in the intestine.

The antimicrobial compound is prepared as an encapsulated powder and combined with carriers as shown in the Table below.

| Ingredient | Percentage by Weight |
|---|---|
| Encapsulated powder | 10–15% |
| Silicon Dioxide (SiO$_2$) | 10–15% |
| Potato Starch | 35–45% |
| Lactose | 15–25% |
| Dextrose | 15–25% |

One 500 mg tablet can be administered to children (ages 5–12 years) every 6 hours for 7 days. Adults can receive 3 tablets every 6 hours for 7 days.

Syrups

Encapsulated powdered antimicrobial compound can be formed as described above and included in a syrup. An example of a syrup formulation is provided in the Table below:

| Ingredient | Percentage by Weight |
|---|---|
| Encapsulated powder | 10–15% |
| Tween 200 | 35–45% |
| Polysorbate | 25–35% |
| Honey Liquid | 15–20% |

Other carriers that can be included in the syrup include flavorings, such as vanilla flavor, strawberry flavor, honey flavor, orange flavor, and etc. Preferably, the carriers are based on sugar products, such as fructose, dextrin and others. Generally, these carriers are added to cover any unpleasant taste (generally bitter) associated with the active ingredients. The syrup can then be used to treat digestive ailments for example, by administering 2 mL of syrup containing 3–5 wt % antimicrobial compound orally every 8 hours.

Liquid Formulation

The antimicrobial compound can be formulated as a liquid for use in treating oral infections in humans by combining antimicrobial compound with carriers as shown in the Table below:

| Ingredient | Percentage by Weight |
|---|---|
| Antimicrobial Compound | 5–10% |
| Polysorbate | 15–25% |
| Propylene Glycol | 70–80% |

The liquid is administered to the area of the infection three times daily until the infection subsides.

Evaporated Solution

The antimicrobial compound can be formulated as an evaporated solution for treating tuberculosis in humans. To prepare this formulation, a liquid solution containing the antimicrobial compound is first prepared as described above. The liquid solution is then evaporated. The evaporated solution is then combined with the carriers shown in the Table below to form a composition that can be inhaled using a mask.

| Ingredient | Percentage by Weight |
|---|---|
| Antimicrobial compound | 15–20% |
| Ethyl alcohol | 15–20% |
| Propylene glycol | 25–35% |
| Double distilled Water | 35–45% |

Three to five (3–5) mL of the formulation is then combined with 500 mL of hot water. The patient inhales the steam for 20 minutes, once a day for 10 to 15 days. The patient can repeat the treatment for 10 more days if the tuberculosis persists.

Intravenous

The antimicrobial compound can be formulated as a solution suitable for intravenous administration or injection into a patient. Such a formulation can be prepared as follows. A liquid antimicrobial composition is prepared as described above. The liquid composition is then combined with a pharmaceutically acceptable carrier such as NaCl as shown in the Table below.

| Ingredient | Percentage by Weight |
|---|---|
| Antimicrobial Compound | 1–2% |
| 0.9% solution of NaCl | 98–99% |

The dosage is approximately 0.25 mL/kg of body weight, for 5–7 days.

Powder

The antimicrobial compound can be formulated as a powder suitable for treating athlete's foot and other external fungal infections. To prepare a powder formulation, a liquid composition is prepared as described above and combined with carriers as shown in the Table below.

| Ingredient | Percentage by Weight |
|---|---|
| Antimicrobial compound | 5–10% |
| Potato Starch | 35–45% |
| CaCO$_3$ | 50–55% |

The powder can be liberally applied to the affected area three (3) times per day for 7 to 10 days.

Gel

The antimicrobial compound can be formulated as a gel for treatment of external infections caused by fungi and bacteria. To prepare a gel, a liquid formulation of the antimicrobial compound is first prepared as described above and then combined with carriers shown in the Table below.

| Ingredient | Percentage by Weight |
|---|---|
| Antimicrobial compound | 5–10% |
| Soya oil | 30–35% |
| Vaselinum album | 55–65% |

The gel is applied to the affected area three times a day for 5 to 7 days.

Shampoo

The antimicrobial compound can be formulated as a shampoo for the treatment of skin infections affecting the head and scalp. The shampoo can be formulated by preparing liquid formulation as described above and then combining the liquid formulation with ingredients to produce a shampoo as shown in the table below.

| Ingredient | Percentage by Weight |
|---|---|
| Antimicrobial compound | 5–10% |
| Shampoo carrier | 40–50% |
| Polyethylene glycol | 45–55% |

The hair and affected scalp should be washed once a day for 10 days with the shampoo formulation. Alternatively, the hair and scalp can be treated with a liquid formulation prepared as described above and combined with corn oil as shown in the Table below.

| Ingredient | Percentage by Weight |
|---|---|
| Antimicrobial Compound | 5–10% |
| Corn Oil | 90–95% |

The liquid formulation can be applied via dropper, 5 drops to the affected area every 8 hours for 3 to 4 days.

E. Illustrative Pharmaceutical Compositions for treatment of Animals other than Humans The antimicrobial compound can be formulated for treating internal and external infections in animals.

Powder

A powder formulation can be prepared by combining antimicrobial compound with silicon dioxide and a coating material as shown in the Table below.

| Ingredient | Percentage by Weight |
|---|---|
| Antimicrobial Compound | 10–15% |
| Silicon Dioxide (SiO$_2$) | 10–15% |
| Coating Material | 75–85% |

This formulation may be administered to a variety of animals, including pigs, horses, sheep, goats, cows, dogs and cats. For example, the formulation can be administered to pigs for the treatment of infections in the large intestines, caused by *Lawsonia intracellularis* and *Treponema hyodysenteriea*. The formulation can be administered to multiple animals by combining the formulation with animal feed (approximately 1000–2000 ppm). Alternately, the formulation can be administered to an individual animal (approximately 0.25 g/kg of body weight)

Powder

The antimicrobial compound may also be used for post surgical use. The following powder formulation could be used for such a purpose:

| Ingredient | Percentage by Weight |
|---|---|
| Antimicrobial Compound | 5–10% |
| CaCO$_3$ | 40–50% |
| Potato Starch | 45–55% |

The post-surgical wound would be treated with the powder to limit the bacteria and/or fungi from growing in the area.

Water Soluble Solution

A water soluble solution can be formulated by combining a liquid formulation of the antimicrobial compound with Polysorbate 80 and polyethylene glycol. Because poultry generally have a short gastro-intestinal tract, it may be preferred to treat poultry with a liquid formulation. An example of such a liquid formulation is shown in the Table below.

| Ingredient | Percentage by Weight |
|---|---|
| Antimicrobial Compound | 10–15% |
| Polysorbate 80 | 35–45% |

-continued

| Ingredient | Percentage by Weight |
|---|---|
| Polyethylene glycol | 45–55% |

The liquid formulation can be included in the drinking water of animals such as poultry or weaning piglets in the amount of 1000–2000 PPM (1000–2000 ml/1000 L water) for 6 days.

Gel

A gel can also be formulated for the treatment of internal infections in animals by combining antimicrobial compound with an emulsifier and propylene glycol as shown below.

| Ingredient | Percentage by Weight |
|---|---|
| Antimicrobial Compound | 10–15% |
| Herbapect (an emulsifier) | 35–45% |
| Propylene glycol | 45–55% |

The gel can be administered to the animal at a dosage of 0.25 g/kg of body weight of young animals.

Liquid Formulation

The antimicrobial compound can also be formulated as a liquid, for example for treating an ear infection in a dog or cat by combining liquid antimicrobial, described above, with sunflower oil and corn oil as shown below.

| Ingredient | Percentage by Weight |
|---|---|
| Antimicrobial Compound | 10–15% |
| Sunflower Oil | 35–45% |
| Corn Oil | 45–55% |

The tonic can be administered at a level of 1 mL/10 kg of body weight of the animal.

Liquid

A liquid formulation may be used for the treatment of skin infections. The following is a method of formulating said liquid:

| Ingredient | Percentage by Weight |
|---|---|
| Antimicrobial Compound | 10–15% |
| Corn Oil | 35–45% |
| Soya oil | 45–55% |

The liquid formulation could be packed in bottles with a dropper for easy application. The formulation should be applied three times daily.

Mastitis

The product of the invention can also be used to treat mastitis. Liquid antimicrobial compound is prepared as shown in the Table below.

| Ingredient | Percentage by Weight |
|---|---|
| Antimicrobial compound | 3–5% |
| Olive oil | 30–40% |
| Silicon Gel | 5–10% |

-continued

| Ingredient | Percentage by Weight |
|---|---|
| Water | 55–60% |
| Vitamin A | 0–1% |

The mixture is then combined with corn oil and Vaselinum album as shown below.

| Ingredient | Percentage by Weight |
|---|---|
| Antimicrobial compound | 5–10% |
| Corn oil | 25–35% |
| Vaselinum album | 60–70% |

The formulation is delivered via a mastitis injector; 10 ml, twice a day to treat cows, and 5 mL, twice a day to treat sheep and goats.

Bolus

The antimicrobial compound can also be formulated as a bolus. An encapsulated powder of the antimicrobial compound is prepared and combined with ethyl cellulose and colloid as shown in the Table below.

| Ingredient | Percentage by Weight |
|---|---|
| Encapsulated powder | 10–15% |
| Ethyl cellulose | 75–85% |
| Colloid | 5–15% |

The bolus can be administered at a level of 10 g/25 kg of the body weight of the animal.

Tablet

The antimicrobial compound can also be formulated as a tablet. First, an encapsulated powder is formed as described above. The encapsulated powder is then combined with colloid as shown in the Table below.

| Ingredient | Percentage by Weight |
|---|---|
| Encapsulated powder | 85–95% |
| Colloid | 5–15% |

The composition can be formulated as a 500 mg tablet which can be administered every 12 hours per 10 kg of body weight of the animal.

Feed Supplement

The antimicrobial compound can also be formulated as a feed supplement. First, an encapsulated powder of the antimicrobial compound is prepared and combined with microelements and vitamins as shown in the Table below.

| Ingredient | Percentage by Weight |
|---|---|
| Encapsulated powder | 45–55% |
| Microelements | 35–45% |
| Vitamins | 5–15% |

The formulation can be added to animal feed at a level of 10 g per day per horse.

Ointment

The antimicrobial compound can be prepared as an ointment to treat skin and sub-surface infections caused by bacteria and fungi. A liquid formulation of the antimicrobial compound is prepared and combined with the ingredients as shown in the Table below.

| Ingredient | Percentage by Weight |
| --- | --- |
| Antimicrobial compound | 5–10% |
| Olive oil | 55–60% |
| Vaselinum album | 35–40% |
| Vitamins A & E | 5,000 IU |

First, the ingredients are combined with the olive oil, in a mixer at 50 RPM for 5 minutes. The mixer is then heated to 75° C. to melt the Vaselinum album. After the Vaselinum album is melted, the active ingredients and olive oil are combined and mixed for 3 minutes at 200 RPM at 75° C. The liquid formulation is then combined with Parafinum liquidum and Vaselinum album.

| Ingredient | Percentage by Weight |
| --- | --- |
| Antimicrobial composition | 10–15% |
| Parafinum liquidum | 35–45% |
| Vaselinum album | 45–55% |

The ointment is applied to the affected area three times daily.

Eczema

Skin eczema on animals can also be treated with the product of the invention. The following formulation would be useful for this application:

| Ingredient | Percentage by Weight |
| --- | --- |
| Antimicrobial Compound | 5–10% |
| Corn Oil | 40–45% |
| Vaselinum album | 45–55% |

The ointment of the above formulation should be applied three times daily to the affected area.

Spray

A spray can also be formulated for the treatment of wounds, and sub-skin infections on animals using the following formulation:

| Ingredient | Percentage by Weight |
| --- | --- |
| Antimicrobial Compound | 10–15% |
| Spray gas carrier | 35–45% |
| Propylene glycol | 45–55% |

The spray can be sprayed on the affected area three times daily.

F. Illustrative Dosages—Animals

Illustrative dosages are provided. The percentage (%) of ointment, spray, liquid, drops indicates the concentration by weight of the active ingredient. Dosages mentioned in ccm or ml refer to the quantity of product (ointment, spray, etc.) used.

Feed Supplement

A microencapsulated powder of antimicrobial compound can be administered to animals as a feed supplement for the treatment of the following pathogens in a variety of animals. The micro-encapsulated powder is used because the indicated pathogens exist at the end of the small intestines and in the beginning of the large intestines. Administration as a feed supplement is preferable for mass treatment of a group of animals.

The dosage levels are different for the different animals. Additionally, if the animals are young, the dosage is higher because of lower feed consumption. The duration of treatment may vary depending on the clinical situation of the farm.

| Pathogen & Animal (age) | Antimicrobial Compound |
| --- | --- |
| *Eschericia coli* and Salmonella spp | |
| weaning piglets (21–25 days) | 2000 PPM |
| weaning piglets (25–30 days) | 1500 PPM |
| weaning piglets (30–35 days) | 1000 PPM |
| weaning piglets (35–42 days) | 750 PPM |
| pigs (42–60 days) | 500 PPM |
| pigs (25 kg–60 kg) | 350 PPM |
| pigs (60 kg–100 kg) | 250 PPM |
| broilers (1–10 days) | 1000 PPM |
| broilers (10–28 days) | 750 PPM |
| broilers (28–37 days) | 500 PPM |
| broilers (37–45 days) | 300 PPM |
| turkey (20–25 days) | 1500 PPM |
| turkey (25 days–4 weeks) | 1000 PPM |
| turkey (4–12 weeks) | 750 PPM |
| egg laying hens | 350 PPM |
| rabbits (30–60 days) | 750 PPM |
| rabbits (60–90 days) | 500 PPM |
| Eimeria spp., Staphylococcus spp | |
| broilers (10–28 days) | 750 PPM |
| egg laying hens | 500 PPM |
| rabbits (30–60 days) | 500 PPM |
| calves (10–30 days) | 1000 PPM |
| *Vibrio coli, Treponema hyodesynteriae, Lawsonia intracellularis* | 750 PPM |
| pigs (30–70 kg) | |
| *Eschericia coli.*, Salmonella spp | |
| Pigs of all categories | 3500 PPM, 7 days |
| Poultry of all categories | 3500 PPM, 7 days |
| Rabbits of all categories | 3000 PPM, 7 days |
| Eimeria spp. (coccidiosis) | |
| Poultry of all categories | 4000 PPM, 7 days |
| Rabbits of all categories | 3500 PPM, 7 days |
| Staphylococcus spp. | |
| Poultry of all categories | 3000 PPM, 5 days |
| Other animals with mass treatment | 2750 PPM, 5 days |
| *Vibrio coli, Treponema hyodesynteriae, Lawsonia intracellularis* | 1500 PPM, 10 days |

Individual Treatment

For the treatment of individual animals, antimicrobial powder can be mixed with water or milk and applied directly to the mouth of the animal. Alternately, antimicrobial powder can be administered as a feed supplement.

*Eschericia Coli* spp

| | |
| --- | --- |
| calves, lambs, young goats, piglets, foals | 200 mg (milligrams)/kg of body weight or 100 mg (milligrams)/Lb. of feed for 3–5 days |

-continued

| Eimeria spp | |
|---|---|
| calves, lambs goats | 150 mg/kg of body weight (7 days) |
| pet birds | 4 g of powder/kg of feed or 2 g of powder/Lb. of feed (7 days) |
| Canine Diarrhea | |
| *Eschericia coli* spp., Proteus etc dogs | 1 500 mg capsule per 10 kg of body weight, every 9 hours till diarrhea stops. |
| Salmonella spp | 2 500 mg capsules per 10 kg, every 8 hours till diarrhea stops |

Cryptosporidiosis in Calves

Cryptosporidiosis is preferably treated using micro-encapsulated (coated) antimicrobial powder as cryptosporidiosis exists at the beginning of the large intestine. Calves of age 5–15 days suffer the most from this disease. It is believed that Cryptosporidia in calves could be prevented by administering 2 capsules containing 6 g antimicrobial compound to calves at 4 days after birth.

| Day 1 of treatment | 3 capsules (or bolus) of 6 g each in the morning 2 capsules (or bolus) of 6 g each after 12 hours |
|---|---|
| Day 2 of treatment | 2 capsules (or bolus) of 6 g each in the morning 2 capsules (or bolus) of 6 g each after 12 hours |
| Day 3 of treatment | Repeat treatment if necessary |

Treatment of Cryptosporidiosis in Lambs and Goats

Lambs and goats may be treated with a capsule (or bolus) containing 1 g of antimicrobial compound made using micro-encapsulated powder. Preferably the animal is administered 2 capsules (boluses) every 12 hours for 2–3 days.

Water Soluble Solution (10%)

The antimicrobial compound can be administered to animals by combining it with their drinking water.

| Eschericia Coli spp. Piglets weaned (21–45 days) Salmonella spp | 1000 PPM |
|---|---|
| Piglets weaned (21–45 days) | 1500 PPM |
| Other pigs categories for all infections | 500 PPM |
| *Eschericia Coli*, Eimeria spp., Campylobacter; Salmonella spp. Poultry of all categories Therapeutic dosage: | 500 PPM |
| Piglets weaned (*Eschericia Coli*): | 1500 PPM for 7 days |
| Pigs (Salmonella spp): | 2000 PPM for 10 days |
| Poultry all categories (*Eschericia Coli*): | 1000 PPM for 7 days |
| Poultry all categories (Salmonella spp): | 1500 PPM for 10 days |
| Poultry all categories (Eimeria spp. Coccidiosis): | 750 PPM for 6 days |

Gel Form of Product 10%

The antimicrobial compound can be administered as a gel. Preferably, the gel is applied directly to the mouth of the animal.

| Therapeutic dosage | |
|---|---|
| *Eschericia Coli*, Eimeria | |
| Piglets, lambs and goats | up to 2 ccm per 10 kg body weight (2–3 days) |
| Calves | up to 2 ccm per 10 kg body weight (2–3 days) |
| Salmonella spp | up to 3 ccm per 10 kg body weight (7–10 days) |
| Pigs, lambs, goats, calves | |
| Foals (intestinal infections of different etiology) | 3 ccm per 10 kg body weight (3 days) |

Emulsion-tonic Form of Product 10%

The antimicrobial compound may be applied, using a tube and pumps, directly to the mouth of a sick animal.

For preventing *Eschericia coli* infection in piglets 1 ml of a 10% emulsion per head at the age of 2 days may be administered. *Eschericia coli* and Clostridium infections in lambs and goats may be prevented by administering 2 ml of a 10% emulsion at the age of 2 days.

A 10% emulsion may be used therapeutically to alleviate *Eschericia coli* infections. In piglets (age 1–3 days), 1 ml of a 10% emulsion may be administered per head for 2 days. For piglets up to an age of 10 days, 2 ml may be administered per head of piglet for 2 days. For lambs and goats 1–5 days old, 2 ml may be administered per head for 2–3 days. For lambs and goats 5–10 days old, 3 ml may be administered per head for 2–3 days.

Topical Infections

Bacterial infections in cows, horses, pigs, sheep, goats caused by Streptococcus spp., Staphylococcus spp., Furunculose can be treated by spraying a 3% solution on the infected skin 3 times per day at a distance of 20 cm from skin for 3–5 days. Alternately, a 3% cream ointment can be applied 3 times per day on the infected skin (2–3 ccm) for 3–5 days. A 3% liquid formulation can be applied 3 times per day on the infected skin (2–5 ccm) for 3–5 days.

Fungal infections on large animals caused by Trichophyton spp., Microsporum spp., and *Candida albicans* can be treated by spraying a 3.5% solution on the infected skin 4 times per day for 5–7 days. Alternately, a 3.5% cream ointment can be applied 4 times per day (3–5 ccm) on the infected skin for 5–7 days.

Pododermatitis-Panaricium in cows and horses caused by Streptococcus spp., Staphylococcus spp., and *Staphylococcus piogenes* can be prevented by spraying a 2% solution on an infected hoof twice a day (3–5 ml) for 5–7 days. Alternately, a 3% liquid solution can be used to wash an infected hoof twice a day (10 ml: 50 Lit. Of water) for 5–7 days.

Bacterial infections in pets caused by Streptococcus spp., Staphylococcus spp., acne, and Furunculosis, can be treated by spraying a 2.5% solution on the infected skin (1–2 ccm) 3 times a day for 6 days. Alternately, a 2.5% ointment can be applied to the infected skin (1–2 ccm) 3 times a day for 6 days. A 2.5% liquid solution can be applied to the infected skin (1–2 ccm) 3 times a day for 6 days.

Fungal infections in pets (cats and dogs) caused by Trichophyton spp., Mycrosporum spp, or *Candid ablicans* can be treated by spraying 1–2 ml of a 3% solution on the infected skin 4 times a day for 7–10 days. Alternately, 1–2 ccm of a 3% ointment can be applied to the infected skin 4 times a day for 7–10 days. 1–2 ml of a 3% liquid solution can be applied to the infected skin 4 times a day for 7–10 days.

Ear Inflammation (otitis)

Bacterial infections in cats and dogs caused by Streptococcus spp can be treated by administering drops (1ml) of a 1% solution to the ear 3 times per day every 8 hours for 7 days. Fungal infections in the ear canal of cats and dogs caused by Trichophytom can be treated with drops (1 ml) of a 2.5% solution 4 times per day for 10 days. Other ear infections, such as Scabies spp can be treated with drops (1.5 ml) of a 3% solution 4 times per day for 10 days.

Eye Infections

Treatment of conjunctivitis (eye infections) caused by bacteria (Streptococcus, Stephylococcus) can be treated with eye drops of a 1% solution (for large animals) 3 times a day for 7 days. For smaller animals (such as cats and dogs) drops of a 0.5% solution can be administered 3 times per day for 5 days.

G. Illustrative Dosages-Humans

Intestinal infections—Bacteria

Bacterial infections of the intestine, such as those caused by *Eschericia coli*, Salmonella, typhimurim, Streptococcus spp., Staphylococcus spp., Dysenteria, Campylobacter spp. can be treated in humans by oral application of the following:

Syrups (3.5%):every 6 hours 2ccm for children up to 3 years for 3–5 days every 6 hours 3ccm for children 3–6 years for 3–5 days every 6 hours 4ccm for children 6–8 years for 3–5 days every 6 hours 5 ccm for children 8–10 years for 3–5 days Capsules: 2 capsules (500 mg/capsule) every 8 hours for children 10–15 years (3–5 days) 3 capsule (500 mg/capsule) per day for 3–5 days for 15 years-adult.

Tablets: same dosages as capsules

Intestinal Infections—Flagellates and Protozoa

Intestinal infections caused by cholera (*Vibrio cholerae*), or Cryptosporidia can be treated with micro-encapsulated capsules or tablets which include micro-encapsulated powder.

Tablets: 1–2 tablets (200 mg) every 6 hours for 3–7 days (children 0–3 years). 1–3 tablets (250 mg) every 6 hours for 3–7 days (children 3–10 years). 2–3 tablets (300 mg) every 6 hours for 3–7 days (10–15 years) 500 mg per 35 kg of body weight, every 6 hours for 3–7 days (adults).

Intestinal Infections—Fungus

Intestinal infections caused by Candida, or Aspergillus spp can be treated using a tablet that includes micro-encapsulated powder. Generally, 500 mg should be administered for each 25 kg for 20–30 days. Every 7 days, pause one day.

Topical Infections

Skin infection in humans caused by Candida, Trichophytom spp., and Microsporum spp can be treated by spraying 1–2 ml of a 3.5% solution on the infected skin 4 times per day for 10–15 days. 1–3 ccm of a 5% cream can be applied to the infected area 3 times per day for 10–15 days. A 3.5% powder can be applied between the toes to treat "athlete's foot" 3 times a day for 5–10 days. A 3.5% soap or shampoo can be used to wash the skin on a foot suffering from "athlete's foot" twice per day using 3 ml of shampoo for each liter of water.

Eye Infections

Infections of the eye caused by bacteria such as Streptococcus, or Staphylococcus, or by traumatic insults can be treated by applying 3–5 drops of a 0.5% solution 3 times per day for 5–7 days. 0.5–1 grams of a 0.5% ointment can be applied to the eye 3 times per day for 5–7 days.

Ear Infections

Ear infections caused by bacteria, fungi and/or parasites can be treated by applying 0.3–1 ml of a 1% solution to the ear 3 times per day for 3–5 days.

III. Method of Use

1. Treating Internal and External Infections

As used herein the terms "treat", "treating" and "treatment" refer to curative therapy, prophylactic therapy, and preventative therapy.

The pharmaceutical composition may be used to treat a variety of microbial infections, including bacterial, fungal, protozoan, yeast, nematodes and other parasitic infections. For example, the pharmaceutical composition may be used to treat internal infections, for example, along the gastrointestinal tract, urinary tract infections (e.g., glomerulonephritis, nephritis, and urocysitis), and endometriosis. Additionally, the pharmaceutical composition may be used to treat external infections, for example, infections of the skin such as panarcium, pododermatitis, and "athlete's foot", sub-skin infections such as tryphophyton, microsporum, Staphylococcus infections, infections caused by other pathogens and hoof infections. The pharmaceutical composition can also be used as an oral disinfectant to treat gingivitis, pharingitis, and other infections and for the treatment of diseases such as tuberculosis, pneumonia, bronchitis, and arthritis. The composition is also suitable for the treatment of acne and eczema.

The pharmaceutical compositions are suitable for treating diseases caused by pathogens such as Cryptosporidia spp., *Serpulina hyodesynteria, Lawsonia intracelluaris,* protozoas, Pasteurella spp., Campylobacter spp., Eimeria spp., Hystomoniais, *Cryptococcus neoformans, Candidia albicans, Eschericia coli*, Kelbsiella spp., *Enterobacter aerogenes, Escherichia coli*, Salmonella spp., for example, *Salmonella typhimurium*, Streptococcus spp., for example, *Streptococcus agalactiae*, Staphylococcus spp., for example, *Staphylococcus aureus, Helicobacter pylori, Mycobacterium tuberculosis*, Trychophyton spp., Microsporum spp., *Candida ablicans*, and *Spherophorus necrophorus*.

The pharmaceutical compositions are also suitable for treating chronic inflammation of the intestines caused by organisms such as Streptococcus spp., Staphylococcus spp., Vibrio, Teniae, Trichinella, Cryptosporidia and others. As used herein, the term "chronic inflammation of the intestine" refers to any condition in which the intestinal mucosa is inflamed for more than 30 days. Symptoms of chronic inflammation of the intestine include diarrhea, and decreased appetite. Preferably, to treat chronic inflammation of the intestine, the antimicrobial compound is formulated as a microcapsule for release in the intestines.

The pharmaceutical compositions are particularly well suited for the treatment of young animals. Young animals frequently suffer from intestinal bacterial, fungi or protozoa species which may cause diarrhea and even death. As used herein, the term "young animals" includes piglets (sucking and weaning of age 1–21 days), broilers (age 1–30 days), calves (age 1–30 days), lambs (age 1–15 days), young goats (age 1–15 days), foals (age 1–10 days), dogs (age 1–15 days), etc.

The antimicrobial composition also increases metabolism, and oxygen absorption (See Example 18). Therefore, the composition can also be administered to an animal, such as a race horse or greyhound, to increase speed.

IV. High Speed Turbo Mixer

Preferably the antimicrobial compounds are formed using a high speed turbo mixer. Preferably the high speed turbo mixer is capable of admixing the organic phenolic compound with the other reactants (e.g., organic acid or Group I salt) at speeds between 200 RMP and 2000 RPM, most preferably about 1500 RPM to 2000 RPM.

An elevational view of a high speed turbo mixer 10 is shown in FIG. 9. The high speed turbo mixer includes a receptacle 20 which has an inner wall 2, an outer wall 1 and a base 5 which define a cavity 4. Preferably, the circumference (or diameter) of the cavity 4 increases as it extends upwards from the base 5. More preferably, the outer 1 wall and the inner 2 wall are configured so that the cavity 4 has a conical volume.

The inner 2 and outer 1 walls of the receptacle 20 can be made of any suitable material including, but not limited to ceramic, metal, plastic and glass. Preferably, the inner 2 and outer 1 walls of the receptacle 20 are formed from a thermally conductive material. More preferably, the walls 1, 2 are formed of a metal material, for example, stainless steel, copper, aluminum, etc., including metal alloys.

Figure 10:
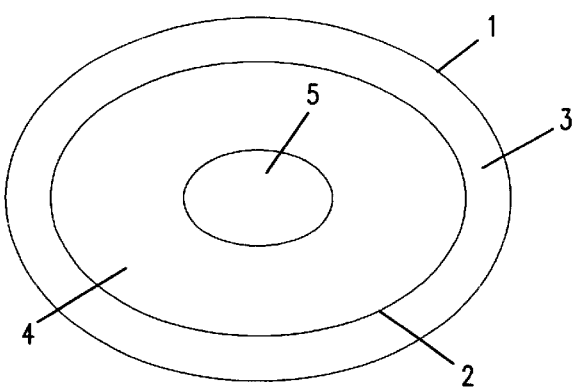
FIG. 10 shows a top sectional view of the mixer in FIG. 9 taken along line 11—11.

Preferably, the inner 2 and outer 1 walls are spaced apart to define a gap 3 as shown in FIG. 10. The gap 3 is configured to receive a heating element (not shown), such as a heating coil. Alternately, the gap 3 may be configured to receive a liquid such as oil or water. In this alternate arrangement, a heating element (not shown) is preferably located at the base 5 of the receptacle 20. The heating element is configured and adapted to heat the inner 2 wall of the receptacle 20 during mixing. Preferably, the inner wall 2 is configured to be heated to a temperature between about 60° C. and 100° C., more preferably between about 75° C. and 80° C. Preferably, the mixer 10 also includes a thermostat (not shown) for maintaining a desired temperature.

The cavity 4 is configured to receive reactants such as organic phenolic compound, Group I salts, organic acids and solvents. Preferably, the receptacle 20 defines a cavity 4 with a volume of about 10 liters to about 50 liters, more preferably about 20 liters to about 30 liters.

The high speed turbo mixer 10 also includes an input conduit 21 and an output conduit 22. The input conduit 21 is configured and arranged for conveying reactants into the cavity 4. The output conduit 22 is configured and arranged for conveying product from the cavity. Preferably, valves (not shown) having open and closed positions are situated to allow reactants to be fed into the cavity 4 and product to be removed from the cavity 4 when in an open position and obstruct passage of reactants or products when in a closed position.

Figure 11:
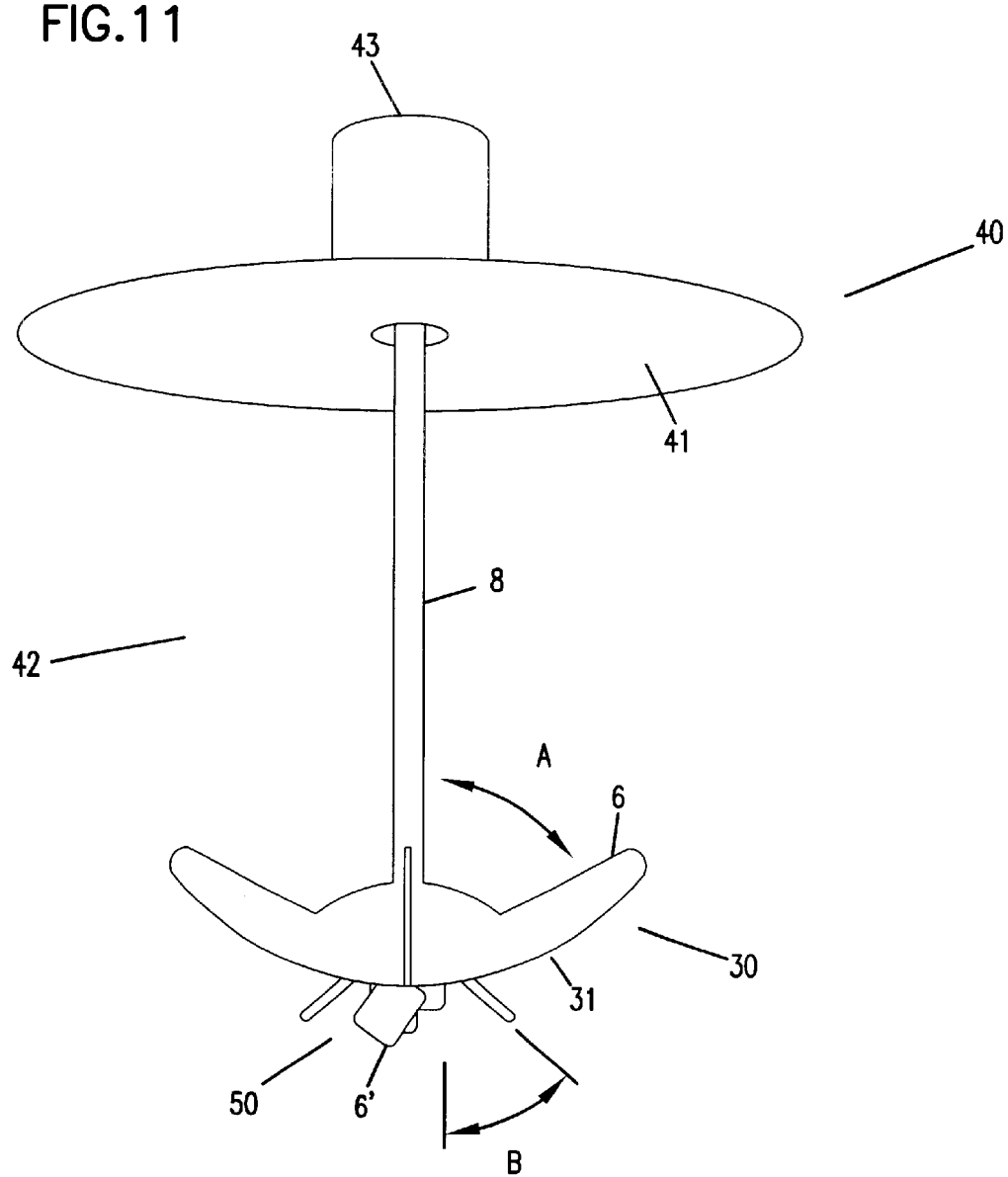
FIG. 11 shows a side elevational drawing of the cover and rotor assembly of the high speed mixer shown in FIG. 9.
Figure 12:
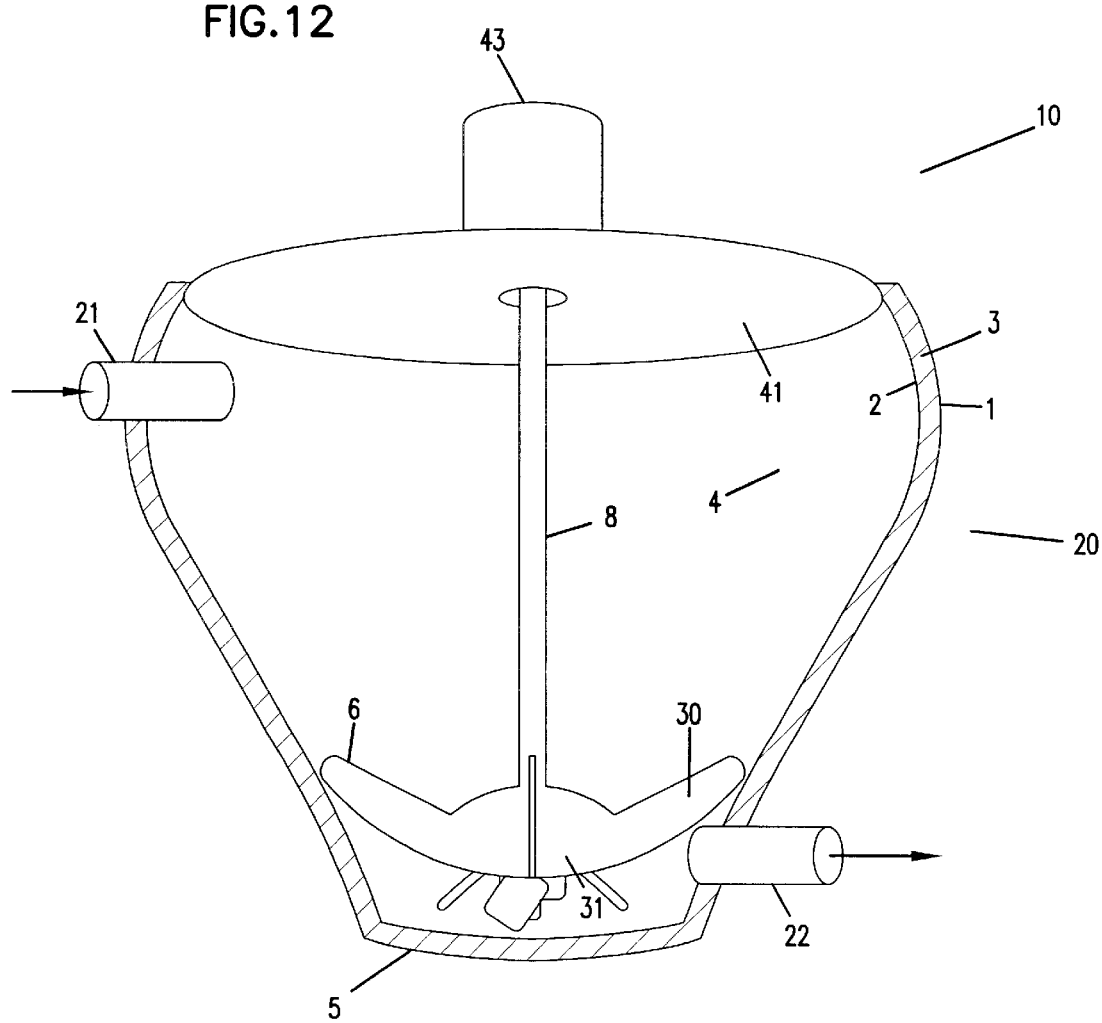
FIG. 12 shows a side elevational cut-away view of the high speed mixer of FIG. 9 with the cover and rotor assembly of FIG. 11 in place.

The high speed turbo mixer 10 also includes a cover and rotor assembly 40 as seen in FIG. 11. The cover and rotor assembly 40 includes a cover 41 which has a circumference sized to fit along the inner wall 2 or outer wall 1 of the receptacle 20 to enclose the cavity 4 during operation. Perpendicular to the cover 41, preferably located in the center of the cover 41, is a rotor assembly 42 which includes a drive shaft 8 and at least one propeller 30.

Preferably the propeller 30 includes a plurality of blades 6, positioned on a central hub 31. Preferably, the blades 6 of the propeller are configured to lie substantially parallel to surface of the inner wall 1. Preferably, the blades form an angle A between about 30° and 90°, more preferably between about 30° and 60° with the drive shaft 8. The blades 6, radiate upwardly and outwardly from the drive shaft 8 towards the inner wall 1 of the receptacle 20 when the cover and rotor assembly 40 is placed on the receptacle 20. Preferably, the propeller 30 comprises from two to six blades 6, most preferably four blades 6. Generally, the blades are about 5 cm to about 15 cm in length, preferably about 5 cm to about 10 cm.

If desired, the rotor assembly 40 may include a plurality of propellers. Preferably, the rotor assembly 40 includes at least a first 30 and a second 50 propeller. Preferably, the first and second propellers are coaxial about the drive shaft 8. The second propeller 50 may be spaced apart from the first propeller 30 (not shown) or may abut the first propeller 30. The second propeller 50 may be positioned proximate the base 5 between the first propeller 30 and the base 5. Alternately, the first propeller 30 may be positioned proximate the base 5 between the second propeller 50 and the base 5. Although the blades 6' of the second propeller 50 can be configured to radiate perpendicular to the drive shaft 8 or radiate outwardly and upwardly towards the inner wall 1 of the receptacle, it is preferred that the blades 6' of the second propeller 50 radiate outward and downward from the drive shaft. Preferably the blades 6' of the second propeller 50 form an angle B between about 30° and 90°, more preferably between about 30° and 60° with the drive shaft 8. Preferably the blades of the second propeller 50 are about 1 cm to about 5 cm in length, more preferably about 2 cm to about 3 cm in length. It is noted that those of skill in the art would recognize that blades may be twisted in addition to being at an angle with respect to the drive shaft 8 to intensify mixing, similar to the blades of a conventional window fan or a airplane propeller. The first 30 and second 50 propellers can rotate in the same direction (i.e., both may rotate in a clockwise direction) when in use or in opposite directions (i.e., one may rotate clockwise and the other may rotate counterclockwise) when in use.

The high speed turbo mixer 10 also includes a motor (not shown). Preferably the motor connects to the housing 43 to power the rotor assembly 42. Generally, the motor is from about 25 watts to about 100 watts, more typically from about 50 watts to about 75 watts. The motor is configured to turn the rotor 30 at a speed between about 200 RPM (revolutions per minute) and 2000 RPM.

V. Working Examples

EXAMPLE 1

Extraction of Isopropyl-l-cresol and Isopropyl Cresol from *Nepeta cataria*

Isopropyl-o-cresol and isopropyl-cresol were extracted from *Nepeta cataria* using a two stage distillation process. In the first stage, dried leaves were extracted using a steam distillation process. After the distillation, the oil is cooled to room temperature for at least 72 hours.

The oil from the steam distillation process was then re-distilled in a second stage distillation process. In the re-distillation, the oil was heated to a temperature of about 186° C. for about 1 hour to remove remaining impurities such as linalool, barneol, pimen, cimen etc. Generally, the impurities have a boiling point of about 150° C. In contrast, both isopropyl-o-cresol and isopropyl-cresol have a boiling point of about 230° C. to 240° C. Thus, a temperature of 180° C. will typically not remove or damage the organic phenolic products.

The oil is again allowed to cool for at least 72 hours to stabilize the oil.

After the oil is cooled, the redistillation is repeated at a temperature of 180° C. for 30 minutes to eliminate almost all of the remaining impurities. The double re-distillation process produced an oil having a purity between 95% and 98%.

After the second re-distillation the oil was allowed to cool for at least 72 hours before production.

EXAMPLE 2

Separation of Isopropyl-o-cresol from Isopropyl-cresol

Isopropyl-o-cresol and isopropyl-cresol were separated by incubating the distilled oil at a temperature of −25° C. for 6 hours. Isopropyl-o-cresol remains as a liquid and isopropyl-cresol is precipitated out as crystals. The two compounds were then separated via filtration.

EXAMPLE 3

Formation of an Antimicrobial Compound using an Organic Acid

An antimicrobial compound was formed by combining the isopropyl-o-cresol from Example 2 with propionic acid and citric acid. 3-{[4-(carboxymethyl)-2-hydroxy-6-isopropylphenoxy]carbonyl}-3-hydroxypentanedioic acid (citro-propiono-cresol or CPC), was formed by combining 50 grams isopropyl-o-cresol with 25 ml propionic acid (90% purity) and 25 ml citric acid (95% purity). The mixture was heated to a temperature of 80° C. and mixed in a high speed turbo mixer for 3 minutes at a speed of 1,000 revolutions per minute.

Upon mixing the isopropyl-o-cresol with the propionic acid and the citric acid, the solution changes from the translucent yellow oil (isopropyl-o-cresol) to a reddish, brown translucent oil evidencing a chemical reaction has taken place.

EXAMPLE 4

Formation of an Organic Compound with an Organic Acid

A second antimicrobial compound was formed by combining the isopropyl-o-cresol from Example 2 with fumaric acid and folic acid. (E)-4-[3-({4-[(4-{[(2-amino-4-hydroxy-2,3-dihydro-6-pteridinyl)methyl]amino}benzoyl)amino]-4-carboxybutanoyl}oxy)-6-hydroxy-2-isopropylphenoxy]-4-oxo-2-butenoic acid (fumo-cresol-folin or FCF), was formed by combining 50 grams isopropyl-o-cresol was combined with 25 ml fumaric acid (90% purity), and 25 ml folic acid (95% purity). The mixture was heated to a temperature of 80° C. and mixed in a high speed turbo mixer for 3 minutes at a speed of 1,000 revolutions per minute.

Similar chemical changes occured as were seen in Example 3 above.

EXAMPLE 5

Formation of an Antimicrobial Compound with a Group I salt

An antimicrobial compound (Sodium para cresol) was formed by combining isopropyl-o-cresol from Example 2 with sodium chloride. 90 grams isopropyl-o-cresol was combined with a solution containing 5 grams sodium chloride (99% purity) and 5 ml ethyl alcohol solution (50% purity). The mixture was heated to a temperature of 80° C. and mixed in a high speed turbo mixer at 1700 RPM (revolution per minute) for 2 minutes.

The ethyl alcohol solution was formed using food grade ethyl alcohol. The 50% solution was formed by combining distilled water and food grade ethyl alcohol in a 1:1 ratio. It was found that the sodium and potassium did not dissolve in pure ethyl alcohol (100%) or 75% ethyl alcohol.

Upon mixing the isopropyl-o-cresol with the sodium chloride and ethyl alcohol solution, the solution changed from the translucent yellow oil (isopropyl-o-cresol) to an opaque, milky, pink solution evidencing that a chemical reaction had taken place.

EXAMPLE 6

Formation of an Antimicrobial Compound with a Group I salt

An antimicrobial compound (Potassium para cresol) was formed by combining isopropyl-o-cresol from Example 2 with potassium chloride. 90 grams isopropyl-o-cresol was combined with a solution containing 5 grams potassium chloride (95% purity) and 5 ml ethyl alcohol solution (50% purity). The mixture heated to a temperature of 80° C. and mixed for 2 minutes at a speed of 500 revolutions per minute.

The ethyl alcohol solution was prepared as in Example 5 above.

Similar chemical changes occurred as were seen in Example 5 above.

EXAMPLE 7

Formation of an Antimicrobial Compound with a Group I salt

An antimicrobial compound (Sodium M cresol) was formed by combining isopropyl-cresol from Example 2 with sodium chloride. 90 grams isopropyl-cresol was combined with a solution containing 5 grams sodium chloride (99% purity) and 5 ml ethyl alcohol solution (50% purity). The mixture was heated to a temperature of 80° C. and mixed in a high speed turbo mixer at 1700 RPM (revolution per minute) for 2 minutes.

The ethyl alcohol solution was prepared as in Example 5 above.

Similar chemical changes occurred as were seen in Example 5 above.

EXAMPLE 8

Formation of an Antimicrobial Compound with a Group I salt

An antimicrobial compound (Potassium M cresol) was formed by combining isopropyl-cresol from Example 2 with potassium chloride. 90 grams isopropyl-cresol was combined with a solution containing 5 grams potassium chloride (95% purity) and 5 ml ethyl alcohol solution (50% purity). The mixture heated to a temperature of 80° C. and mixed for 2 minutes at a speed of 500 revolutions per minute.

The ethyl alcohol solution was prepared as in Example 5 above.

Similar chemical changes occurred as were seen in Example 5 above.

EXAMPLE 9

Unmodified Essential Oil

Essential oil was extracted from *Oreganum vulgaris* by steam distillation essentially as described in PCT/NL96/

00210. Briefly, the leaves and blossoms of the plants were dried and placed in a distiller. A water source positioned under the leaves and blossoms was heated to about 100° C. under a pressure of about 20 bar for about 2 to about 3 hours. The extracted oil was removed from the distillation column and allowed to cool for at least 72 hours.

EXAMPLE 10

Formulation

A 10% liquid formulation was prepared by combining 50 ml organic phenolic sodium salt (sodium para cresol) from Example 5 and 50 ml organic phenolic potassium salt (potassium para cresol) from Example 6. The combination was mixed at room temperature for 5 minutes at a speed of 350 RPM.

EXAMPLE 11

Formulation

A 10% liquid formulation was prepared by combining 48.5 ml organic phenolic sodium salt (sodium para cresol-SPC) from Example 5; 48.5 ml organic phenolic potassium salt (potassium para cresol-PPC) from Example 6; 1.5 ml organic phenolic sodium salt (sodium M cresol-SMC) from Example 7; 1.5 ml organic phenolic potassium salt (potassium M cresol-PMC) from Example 8; and 900 ml of a liquid carrier. The liquid carrier contained Polysorbate 80 (30wt %) as an emulsifier, ethyl alcohol (20 wt %) and polyethylene glycol (40wt %). The combination was mixed at room temperature for 7 minutes at a speed of 1700 RPM to form a final (10%) solution containing a ratio of SPC & PPC to SMC & PMC of 97: 3.

EXAMPLE 12

In vitro testing

An in vitro test was performed to demonstrate the antibacterial activity of the antimicrobial product. Four groups were used for the test. The first group (A) was a negative control group to which no antimicrobial agent was provided. The second group (B) was a positive control group to which a formulation containing 10% of an unmodified essential oil from Oreganum vulgaris was administered (described in Example 9). The third group (C) was an experimental group to which the formulation described in Example 10 was administered. The fourth group (D) was an experimental group to which the formulation described in Example 11 was administered.

A. Microorganism Culture

On Day 1, 0.1 ml from a culture of liquid agar containing Eschericia coli was transferred into 10 ml of a second agar solution. On Day 2, 0.1 ml of the second liquid agar culture was again transferred to 10 ml of a third agar solution. On day 3, 0.2 milliliter of the culture in the third liquid agar solution was transferred to a flask containing 80 milliliter melted agar at a temperature of 45° C.

B. Testing Protocol

After incubating the culture in the flask for 24 hours, 4 culture plates (petri dishes) were filled with 10 ml of the agar solution. 3 of these petri dishes were used to test the three active ingredients (B, C and D), 1 petri dish was used as a negative control (A). A ring encompassing 50 millimeter was positioned in the center of each petri dish (except for the negative control). The rings were used to create a defined area of the agar solution containing bacteria species. 0.1 ml of one of the three active ingredients (B, C or D) was added to one of the three petri dishes. All four plates were then stored at 5° C. for one hour. After that, all four petri dishes were incubated for 24 hours at a temperature of 37° C. After 24 hours, the rings were removed and the inhibitory effect of each active ingredient was examined by measuring the inhibition zone (described in millimeters) of each plate within the rings. In the case of complete inhibition, the whole area within ring is free from any of bacterial species.

The identical protocol was repeated with cultures of Salmonella typhimurim and Staphylococcus aureus.

C. Results

In all of three negative control petri dishes, the bacterial species grew throughout the whole plate. This indicates that the cultures were viable. The results from the other petri dishes are shown below:

| Name of bacterial species | Inhibition zones in mm | | |
|---|---|---|---|
| | B | C | D |
| Eschericia Coli | 28 | 35 | 43 |
| Salmonella typhymurium | 13 | 17 | 20 |
| Staphylococcus aureus | 26 | 31 | 39 |

D. Conclusion

All three active ingredients demonstrate a cidal effect against all three pathogens. The largest inhibition zones for each of bacterial species was produced using formulation (D).

EXAMPLE 13

Comparative Testing

Isopropyl-o-cresol (95% purity) was obtained as described in Examples I and 2. A 50% solution of isopropyl-o-cresol was prepared by combining 50 grams of isopropyl-o-cresol with 25 ml citric and propionic acid.

An antimicrobial compound containing isopropyl-o-cresol was prepared as described in Examples 3 and 4.

Each compound was administered to a culture of hepatocytes. Cell death was observed by monitoring whether or not the cells multiplied. If the cells did not divide, it was assumed that the composition had a suppressive effect on genes and was considered to be matagenic, carcinogenic and/or teratogenic (dangerous for pregnant women and animals and fetus)."

It has been found that the antimicrobial compound formed by reacting an organic phenolic compound with an organic acid or salt results in a compound with substantially greater antimicrobial activity than the organic phenolic compound alone. For example, when the microorganism culture was contacted with isopropyl-o-cresol alone the cells died within 6–8 hours after contact. When the microorganism culture was contacted with isopropyl-o-cresol combined with an organic acid to form a solution (without chemical modification of either species), the microorganisms died within 3–4 hours after exposure. When the microorganism culture was contacted with an antimicrobial compound containing isopropyl-o-cresol reacted with propionic and citric acids (50:50), the organisms died within 5–10 minutes after being contacted with the antimicrobial compound.

EXAMPLE 14

In Vivo Testing—Diarrhea

A. Protocol

Three adult humans, one male age 63 years and two females, ages 47 and 51 years suffering from diarrhea were administered two to three 500 mg capsules containing 10% essential oil formulated as described in Example 9 (referred to as product A) and the formulation described in Example 11 (referred to as product B) 3–4 times per day.

B. Results

When administered formula (A) the individuals experienced negative side effects including a strong gurgling and unpleasant feeling in their stomach. When administered formula (B), the side effects disappeared.

EXAMPLE 15

In Vivo Testing—Cryptosporidia

In vivo tests have been done to determine the efficacy of the antimicrobial composition as a preventative treatment against Cryptosporidia.

Forty seven calves (4 days old) were administered either a control antibiotic containing Buytril (active ingredient: enrofloxacine) or the formulation described in Example 10 encapsulated as described below. The test dosage was 2 capsules per day per calf.

Encapsulation Process

The antimicrobial compound describe in Example 10 was encapsulated using fluid bed equipment (Vector Corporation, Marion, Iowa). First, the antimicrobial formulation from Example 11 was combined in the fluid bed mixer with the ingredients shown in the table below for 20 minutes at a temperature of 87° C.

| Ingredient | Percentage by weight |
| --- | --- |
| Antimicrobial Compound | 10% |
| Corn Starch | 35% |
| Dextrose | 40% |
| Calcium Carbonate | 5% |
| Sodium Bicarbonate | 5% |
| Silicon Dioxide ($SiO_2$) | 5% |

After 20 minutes, soybean oil was added to the fluid bed mixer and mixed for 10 minutes to form a soybean oil layer on the antimicrobial powder. After the soybean oil as dry, ethyl cellulose was added to the mixer and mixed for 10 minutes to form an ethyl cellulose layer. The process was repeated to form a 6 gram tablet with 6 layers (i.e., 3 soybean oil layers and 3 ethyl cellulose layers)

The success rate for preventing cryptosporidiosis using formulation (A) was 30%. In contrast, the success rate for treating cryptosporidiosis using formulation (B) was over 95%.

EXAMPLE 16

Synergy

The efficacy of the formulation described in Example 11 was compared to the efficacy of the formulation described in Example 10.

35 piglets, age 3 days, with diarrhea caused by *Eschericia coli* infection were treated by pumping 1 ml of a 10% liquid solution containing the formulation of Example 10 directly into the piglet's mouth every 6 hours.

After the first treatment (i.e., after 6 hours) 22 (62.85%) of the treated piglets were free from diarrhea. The remaining 13 pigs were treated a second time. After the second treatment, 6 more piglets were free from diarrhea. The remaining 7 piglets were then treated a third time. After the third treatment 3 more piglets were free from diarrhea. After the fourth treatment, the remaining 4 piglets were free from diarrhea.

37 piglets, age 3 days, were treated as described above, with the formulation from Example 11. After first treatment, 29 piglets (78.37%) where free from diarrhea. After the second treatment, the remaining 8 piglets (21.63%) where free from diarrhea.

EXAMPLE 17

Carcinogenicity

A solution containing 1 wt % to 10 wt % of the formulation described in Example 11 was added every 8 hours for 10 months to a culture of hepatocytes. If exposed to a carcinogenic or mutagenic compound, the hepatocytes do not divide properly. The culture was examined every 10 days for 10 months using an electronic microscope at no less than 1000 times magnification. At this magnification, chromosomal aberrations, if present, are visible. No chromosomal aberrations were detected.

EXAMPLE 19

Fungi 11 cows and 28 dogs were treated with a solution containing 3 wt % of the formulation described in Example 11 for infections caused by fungi from the species Candida, Tryhophyton and Microsporum. The 3 wt % solution was administered by spraying the infected skin 3 times a day with 2 ml of solution.

The presence of the fungi was detected using microscopy. Candida species disappeared after 7 days of treatment. Microsporum and Tryhophyton infection disappeared after 5 days a treatment.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A pharmaceutical composition for treating a microbial infection in an animal, said composition comprising:
   (a) antimicrobial compound, wherein said antimicrobial compound comprises an organic phenolic compound chemically reacted with a Group I salt; and
   (b) a pharmaceutically acceptable carrier.

2. The pharmaceutical composition of claim 1 wherein the organic phenolic compound is selected from the group consisting of isopropyl-o-cresol, isopropyl-cresol and combinations thereof.

3. The pharmaceutical composition of claim 1 wherein the Group I salt is a Group I chloride salt.

4. The pharmaceutical composition of claim 3 wherein the Group I salt is selected from the group consisting of sodium chloride, potassium chloride and combinations thereof.

5. The pharmaceutical composition of claim 1 wherein the antimicrobial compound comprises isopropyl-o-cresol and isopropyl-cresol chemically reacted with sodium chloride and potassium chloride.

6. The pharmaceutical composition of claim 1 comprising 10% antimicrobial compound.

7. The pharmaceutical composition of claim 1 wherein the antimicrobial compound comprises sodium-para-cresol, potassium-para-cresol, sodium-M-cresol and potassium-M-cresol.

8. The pharmaceutical composition of claim 1 wherein the antimicrobial compound comprises 97 wt % sodium-para-cresol and potassium-para-cresol and 3 wt % sodium-M-cresol and potassium-M-cresol.

9. The pharmaceutical composition of claim 1 wherein the microbial infection is selected from the group consisting of a bacterial infection, fungal infection, protozoan infection and yeast infection.

10. The pharmaceutical composition of claim 1 wherein the animal is selected from the group consisting of humans, horses, cows, pigs, sheep, goats, rabbits, dogs, cats, chickens, turkeys, ducks and birds.

11. A method for treating a microbial infection in an animal, said method comprising:
(a) administering to the animal an antimicrobial compound, wherein said antimicrobial compound comprises an organic phenolic compound chemically reacted with a Group I salt.

12. The method of claim 11 wherein the organic phenolic compound is selected from the group consisting of isopropyl-o-cresol, isopropyl-cresol and combinations thereof.

13. The method of claim 11 wherein the Group I salt is a Group I chloride salt.

14. The method of claim 13 wherein the Group I salt is selected from the group consisting of sodium chloride, potassium chloride and combinations thereof.

15. The method of claim 11 wherein the antimicrobial compound comprises isopropyl-o-cresol and isopropyl-cresol chemically reacted with sodium chloride and potassium chloride.

16. The method of claim 11 wherein the antimicrobial compound comprises sodium-para-cresol, potassium-para-cresol, sodium-M-cresol and potassium-M-cresol.

17. The method of claim 11 wherein the antimicrobial compound comprises 97 wt % sodium-para-cresol and potassium-para-cresol and 3 wt % sodium-M-cresol and potassium-M-cresol.

18. The method of claim 11 wherein the microbial infection is selected from the group consisting of a bacterial infection, fungal infection, protozoan infection and yeast infection.

19. The method of claim 11 wherein the animal is selected from the group consisting of humans, horses, cows, pigs, sheep, goats, rabbits, dogs, cats, chickens, turkeys, ducks and birds.

20. A pharmaceutical composition for treating a microbial infection in an animal, said composition comprising:

(a) an antimicrobial compound, wherein said antimicrobial compound comprises an organic phenolic compound;

(b) a Group I cation; and (c) a pharmaceutically acceptable carrier.

21. The pharmaceutical composition of claim 20 wherein the Group I cation is part of a Group I salt.

22. The pharmaceutical composition of claim 21 wherein the Group I salt is a Group I chloride salt.

23. The pharmaceutical composition of claim 21 wherein the Group I salt is a Group I hydroxide salt.

* * * * *

UNITED STATES PATENT AND TRADEMARK OFFICE
CERTIFICATE OF CORRECTION

PATENT NO.     : 6,414,036 B1
DATED          : July 2, 2002
INVENTOR(S)    : Ninkov It is certified that error appears in the above-identified patent and that said Letters Patent is hereby corrected as shown below:

<u>Column 2,</u>
Line 3, "corticum" should read -- cortiucm --
Line 21, "sop.," should read -- spp., --
Line 27, "Micromenia" should read -- Micromeria --

Signed and Sealed this

Eleventh Day of February, 2003

JAMES E. ROGAN
*Director of the United States Patent and Trademark Office*